US009234888B2

(12) United States Patent
Linder et al.

(10) Patent No.: US 9,234,888 B2
(45) Date of Patent: Jan. 12, 2016

(54) FLUIDIC CONNECTORS AND MICROFLUIDIC SYSTEMS

(71) Applicant: OPKO Diagnostics, LLC, Woburn, MA (US)

(72) Inventors: Vincent Linder, Tewksbury, MA (US); David Steinmiller, Cambridge, MA (US); Samuel K. Sia, New York, NY (US)

(73) Assignee: OPKO Diagnostics, LLC, Woburn, MA (US)

( * ) Notice: Subject to any disclaimer, the term of this patent is extended or adjusted under 35 U.S.C. 154(b) by 0 days.

(21) Appl. No.: 14/554,712

(22) Filed: Nov. 26, 2014

(65) Prior Publication Data

US 2015/0079606 A1 Mar. 19, 2015

Related U.S. Application Data

(60) Continuation of application No. 14/222,125, filed on Mar. 21, 2014, which is a continuation of application No. 13/765,042, filed on Feb. 12, 2013, now Pat. No. 8,802,445, which is a division of application No.
(Continued)

(51) Int. Cl.
*G01N 15/06* (2006.01)
*G01N 33/00* (2006.01)
(Continued)

(52) U.S. Cl.
CPC .......... *G01N 33/5302* (2013.01); *B01L 3/5027* (2013.01); *B01L 3/563* (2013.01);
(Continued)

(58) Field of Classification Search
CPC ........ G01N 15/06; G01N 33/00; G01N 33/48
USPC ......... 422/502, 503, 504, 507, 509, 511, 512, 422/554; 436/43, 180, 174
See application file for complete search history.

(56) References Cited

U.S. PATENT DOCUMENTS 3,735,640 A 5/1973 Chizhov et al.
4,318,994 A 3/1982 Meyer et al.
(Continued)

FOREIGN PATENT DOCUMENTS

CN 1157639 A 8/1997
EP 0 110 771 B1 3/1988
(Continued)

OTHER PUBLICATIONS

International Search Report and Written Opinion for PCT/US2008/005577 mailed Apr. 3, 2009.
(Continued)

*Primary Examiner* — Brian J Sines
(74) *Attorney, Agent, or Firm* — Wolf, Greenfield & Sacks, P.C.

(57) ABSTRACT

Fluidic connectors, methods, and devices for performing analyses (e.g., immunoassays) in microfluidic systems are provided. In some embodiments, a fluidic connector having a fluid path is used to connect two independent channels formed in a substrate so as to allow fluid communication between the two independent channels. One or both of the independent channels may be pre-filled with reagents (e.g., antibody solutions, washing buffers and amplification reagents), which can be used to perform the analysis. These reagents may be stored in the channels of the substrate for long periods amounts of time (e.g., 1 year) prior to use.

11 Claims, 20 Drawing Sheets

Related U.S. Application Data

13/467,653, filed on May 9, 2012, now Pat. No. 8,409,527, which is a continuation of application No. 12/113,503, filed on May 1, 2008, now Pat. No. 8,202,492.

(60) Provisional application No. 60/927,640, filed on May 4, 2007.

(51) Int. Cl.
  *G01N 33/48* (2006.01)
  *G01N 33/53* (2006.01)
  *B01L 3/00* (2006.01)

(52) U.S. Cl.
  CPC .......... *B01L 3/565* (2013.01); *G01N 33/5304* (2013.01); *G01N 33/5306* (2013.01); *B01L 2200/025* (2013.01); *B01L 2200/027* (2013.01); *B01L 2200/10* (2013.01); *B01L 2200/16* (2013.01); *B01L 2300/0672* (2013.01); *B01L 2300/0861* (2013.01); *B01L 2400/049* (2013.01); *Y10T 403/22* (2015.01); *Y10T 436/11* (2015.01); *Y10T 436/25* (2015.01); *Y10T 436/2575* (2015.01)

(56) References Cited

U.S. PATENT DOCUMENTS

| | | |
|---|---|---|
| 4,517,302 A | 5/1985 | Saros |
| 4,918,025 A | 4/1990 | Grenner |
| 4,963,498 A | 10/1990 | Hillman et al. |
| 5,051,237 A | 9/1991 | Grenner et al. |
| 5,219,762 A | 6/1993 | Katamine et al. |
| 5,234,813 A | 8/1993 | McGeehan et al. |
| 5,268,147 A | 12/1993 | Zabetakis et al. |
| 5,286,454 A | 2/1994 | Nilsson et al. |
| 5,376,252 A | 12/1994 | Ekström et al. |
| 5,478,751 A | 12/1995 | Oosta et al. |
| 5,486,335 A | 1/1996 | Wilding et al. |
| 5,571,410 A | 11/1996 | Swedberg et al. |
| 5,635,358 A | 6/1997 | Wilding et al. |
| 5,637,469 A | 6/1997 | Wilding et al. |
| 5,726,026 A | 3/1998 | Wilding et al. |
| 5,731,212 A | 3/1998 | Gavin et al. |
| 5,866,345 A | 2/1999 | Wilding et al. |
| 5,876,675 A | 3/1999 | Kennedy |
| 5,942,443 A | 8/1999 | Parce et al. |
| 5,955,028 A | 9/1999 | Chow |
| 5,957,579 A | 9/1999 | Kopf-Sill et al. |
| 6,019,944 A | 2/2000 | Buechler |
| 6,042,709 A | 3/2000 | Parce et al. |
| 6,046,056 A | 4/2000 | Parce et al. |
| 6,103,199 A | 8/2000 | Bjornson et al. |
| 6,136,272 A | 10/2000 | Weigl et al. |
| 6,146,489 A | 11/2000 | Wirth |
| 6,146,589 A | 11/2000 | Chandler |
| 6,168,948 B1 | 1/2001 | Anderson et al. |
| 6,176,962 B1 | 1/2001 | Soane et al. |
| 6,184,029 B1 | 2/2001 | Wilding et al. |
| 6,186,660 B1 | 2/2001 | Kopf-Sill et al. |
| 6,207,369 B1 | 3/2001 | Wohlstadter et al. |
| 6,209,928 B1 | 4/2001 | Benett et al. |
| 6,214,560 B1 | 4/2001 | Yguerabide et al. |
| 6,238,538 B1 | 5/2001 | Parce et al. |
| 6,241,560 B1 | 6/2001 | Furusawa et al. |
| 6,251,343 B1 | 6/2001 | Dubrow et al. |
| 6,274,337 B1 | 8/2001 | Parce et al. |
| 6,296,020 B1 | 10/2001 | McNeely et al. |
| 6,319,476 B1 | 11/2001 | Victor et al. |
| 6,331,439 B1 | 12/2001 | Cherukuri et al. |
| 6,333,200 B1 | 12/2001 | Kaler et al. |
| 6,361,958 B1 | 3/2002 | Shieh et al. |
| 6,413,782 B1 | 7/2002 | Parce et al. |
| 6,416,642 B1 | 7/2002 | Alajoki et al. |
| 6,429,025 B1 | 8/2002 | Parce et al. |
| 6,432,720 B2 | 8/2002 | Chow |
| 6,479,299 B1 | 11/2002 | Parce et al. |
| 6,488,872 B1 | 12/2002 | Beebe et al. |
| 6,488,894 B1 | 12/2002 | Miethe et al. |
| 6,488,896 B2 | 12/2002 | Weigl et al. |
| 6,495,104 B1 | 12/2002 | Unno et al. |
| 6,536,477 B1 | 3/2003 | O'Connor et al. |
| 6,551,841 B1 | 4/2003 | Wilding et al. |
| 6,557,427 B2 | 5/2003 | Weigl et al. |
| 6,610,499 B1 | 8/2003 | Fulwyler et al. |
| 6,613,512 B1 | 9/2003 | Kopf-Sill et al. |
| 6,613,525 B2 | 9/2003 | Nelson et al. |
| 6,620,625 B2 | 9/2003 | Wolk et al. |
| 6,632,619 B1 | 10/2003 | Harrison et al. |
| 6,638,482 B1 | 10/2003 | Ackley et al. |
| 6,656,430 B2 | 12/2003 | Sheppard, Jr. et al. |
| 6,660,367 B1 | 12/2003 | Yang et al. |
| 6,669,831 B2 | 12/2003 | Chow et al. |
| 6,705,357 B2 | 3/2004 | Jeon et al. |
| 6,709,869 B2 | 3/2004 | Mian et al. |
| 6,716,620 B2 | 4/2004 | Bashir et al. |
| 6,729,352 B2 | 5/2004 | O'Connor et al. |
| 6,742,661 B1 | 6/2004 | Schulte et al. |
| 6,761,962 B2 | 7/2004 | Bentsen et al. |
| 6,780,584 B1 | 8/2004 | Edman et al. |
| 6,794,197 B1 | 9/2004 | Indermuhle et al. |
| 6,818,184 B2 | 11/2004 | Fulwyler et al. |
| 6,827,095 B2 | 12/2004 | O'Connor et al. |
| 6,828,143 B1 | 12/2004 | Bard |
| 6,830,936 B2 | 12/2004 | Anderson et al. |
| 6,858,185 B1 | 2/2005 | Kopf-Sill et al. |
| 6,875,403 B2 | 4/2005 | Liu et al. |
| 6,878,271 B2 | 4/2005 | Gilbert et al. |
| 6,878,755 B2 | 4/2005 | Singh et al. |
| 6,906,797 B1 | 6/2005 | Kao et al. |
| 6,949,377 B2 | 9/2005 | Ho |
| 6,953,550 B2 | 10/2005 | Sheppard, Jr. et al. |
| 6,982,787 B1 | 1/2006 | Wapner et al. |
| 6,989,128 B2 | 1/2006 | Alajoki et al. |
| 7,005,292 B2 | 2/2006 | Wilding et al. |
| 7,015,046 B2 | 3/2006 | Wohlstadter et al. |
| 7,018,830 B2 | 3/2006 | Wilding et al. |
| 7,046,357 B2 | 5/2006 | Weinberger et al. |
| 7,067,263 B2 | 6/2006 | Parce et al. |
| 7,087,148 B1 | 8/2006 | Blackburn et al. |
| 7,091,048 B2 | 8/2006 | Parce et al. |
| 7,182,371 B1 | 2/2007 | Renzi |
| 7,276,330 B2 | 10/2007 | Chow et al. |
| 7,475,916 B2 | 1/2009 | Muller et al. |
| 7,513,535 B2 | 4/2009 | Charles et al. |
| 7,524,462 B2 | 4/2009 | Leonard et al. |
| 7,598,091 B2 | 10/2009 | Wang |
| 7,611,616 B2 | 11/2009 | Cohen et al. |
| 7,736,890 B2 | 6/2010 | Sia et al. |
| 7,934,519 B2 | 5/2011 | Zantl |
| 8,000,762 B2 | 8/2011 | Calasso et al. |
| 8,030,057 B2 | 10/2011 | Linder et al. |
| 8,202,492 B2 | 6/2012 | Linder et al. |
| 8,282,896 B2 | 10/2012 | Facer et al. |
| 8,329,118 B2 | 12/2012 | Padmanabhan et al. |
| 8,389,272 B2 | 3/2013 | Linder et al. |
| 8,409,527 B2 | 4/2013 | Linder et al. |
| 8,475,737 B2 | 7/2013 | Linder et al. |
| 8,574,924 B2 | 11/2013 | Sia et al. |
| 8,580,569 B2 | 11/2013 | Linder et al. |
| 8,591,829 B2 | 11/2013 | Taylor et al. |
| 8,633,013 B2 | 1/2014 | Kaiser et al. |
| 8,765,062 B2 | 7/2014 | Linder et al. |
| 8,932,523 B2 | 1/2015 | Linder et al. |
| 2001/0048637 A1 | 12/2001 | Weigl et al. |
| 2002/0001818 A1 | 1/2002 | Brock |
| 2002/0019059 A1 | 2/2002 | Chow et al. |
| 2002/0071788 A1 | 6/2002 | Fujii et al. |
| 2002/0092767 A1 | 7/2002 | Bjornson et al. |
| 2002/0142618 A1 | 10/2002 | Parce et al. |
| 2002/0199094 A1 | 12/2002 | Strand et al. |
| 2003/0012697 A1 | 1/2003 | Hahn et al. |
| 2003/0082081 A1 | 5/2003 | Fouillet et al. |
| 2003/0118486 A1 | 6/2003 | Zhou et al. |

(56) References Cited

U.S. PATENT DOCUMENTS

| | | |
|---|---|---|
| 2003/0124623 A1 | 7/2003 | Yager et al. |
| 2003/0138969 A1 | 7/2003 | Jakobsen et al. |
| 2003/0207328 A1 | 11/2003 | Yguerabide et al. |
| 2004/0077074 A1 | 4/2004 | Ackley et al. |
| 2004/0115094 A1 | 6/2004 | Gumbrecht et al. |
| 2004/0195728 A1 | 10/2004 | Slomski et al. |
| 2004/0228771 A1 | 11/2004 | Zhou et al. |
| 2005/0118073 A1 | 6/2005 | Facer et al. |
| 2005/0161669 A1 | 7/2005 | Jovanovich et al. |
| 2005/0221281 A1 | 10/2005 | Ho |
| 2005/0238545 A1 | 10/2005 | Parce et al. |
| 2005/0255003 A1 | 11/2005 | Summersgill et al. |
| 2006/0002827 A1 | 1/2006 | Curcio et al. |
| 2006/0094119 A1 | 5/2006 | Ismagilov et al. |
| 2006/0257992 A1 | 11/2006 | McDevitt et al. |
| 2006/0275852 A1 | 12/2006 | Montagu |
| 2007/0048189 A1 | 3/2007 | Cox et al. |
| 2007/0298433 A1 | 12/2007 | Sia et al. |
| 2008/0085219 A1 | 4/2008 | Beebe et al. |
| 2008/0248590 A1 | 10/2008 | Gulliksen et al. |
| 2008/0280365 A1 | 11/2008 | Grumann et al. |
| 2009/0019953 A1 | 1/2009 | Bommarito et al. |
| 2010/0158756 A1 | 6/2010 | Linder et al. |
| 2010/0196207 A1 | 8/2010 | Steinmiller et al. |
| 2010/0233038 A1 | 9/2010 | Park et al. |
| 2012/0269701 A1 | 10/2012 | Linder et al. |
| 2013/0157286 A1 | 6/2013 | Linder et al. |
| 2014/0023565 A1 | 1/2014 | Taylor et al. |
| 2014/0038166 A1 | 2/2014 | Linder et al. |
| 2014/0038167 A1 | 2/2014 | Linder et al. |
| 2014/0134603 A1 | 5/2014 | Sia et al. |
| 2014/0234180 A1 | 8/2014 | Linder et al. |
| 2015/0086997 A1 | 3/2015 | Linder et al. |

FOREIGN PATENT DOCUMENTS

| | | |
|---|---|---|
| EP | 0 643 307 A1 | 3/1995 |
| EP | 1 054 259 A1 | 11/2000 |
| EP | 1 946 830 A1 | 7/2008 |
| EP | 2 071 026 A1 | 6/2009 |
| JP | 2006-517652 A | 7/2006 |
| JP | 2007-017354 A | 1/2007 |
| JP | 2007-500850 A | 1/2007 |
| WO | WO 91/01003 A | 1/1991 |
| WO | WO 95/26796 | 10/1995 |
| WO | WO 96/14934 | 5/1996 |
| WO | WO 02/22250 A2 | 3/2002 |
| WO | WO 03/054513 A2 | 7/2003 |
| WO | WO 2004/022233 A1 | 3/2004 |
| WO | WO 2004/061418 A2 | 7/2004 |
| WO | WO 2004/087951 A2 | 10/2004 |
| WO | WO 2004/087951 A3 | 10/2004 |
| WO | WO 2004/105946 A2 | 12/2004 |
| WO | WO 2005/056186 A1 | 6/2005 |
| WO | WO 2005/072858 | 8/2005 |
| WO | WO 2006/018044 A1 | 2/2006 |
| WO | WO 2006/056787 A1 | 6/2006 |
| WO | WO 2006/113727 A2 | 10/2006 |
| WO | WO 2008/118098 A1 | 10/2008 |
| WO | WO 2008/123112 A1 | 10/2008 |
| WO | WO 2008/137008 A2 | 11/2008 |
| WO | WO 2008/005577 A2 | 5/2009 |

OTHER PUBLICATIONS

International Preliminary Report on Patentability for PCT/US2008/005577 mailed May 10, 2009.

Ahn, C. et al., "Disposable Smart Lab on a Chip for Point-of-Care Clinical Diagnostics", *Proceedings of the IEEE*, vol. 92, No. 1, pp. 154-173 (2004).

Andersson, et al., "Micromachined flow-through filter-chamber for chemical reactions on beads", *Sensors and Actuators*, vol. B67, pp. 203-208 (2000).

Atencia, J et al., "Capillary inserts in microcirculatory systems", *Lab Chip*, 6, 575-577 (2006).

Atencia, J. et al. "Steady flow generation in microcirculatory systems", *Lab Chip*, 6, 567-574 (2006).

Darion, et al., "Chemical sensing using an integrated microfluidic system based on the Berthelot reaction", *Sensors and Actuators B*, vol. 76, pp. 235-243 (2001).

Dodge, et al., "Electrokinetically Driven Microfluidic Chips with Surface-Modified Chambers for Heterogeneous Immunoassays", *Anal. Chem.*, vol. 73, pp. 3400-3409 (2001).

Fredrickson, C. et al., "Macro-to-micro interfaces for microfluidic devices", *Lab Chip*, 4, 526-533 (2004).

Grodzinski, P. et al., "A Modular Microfluidic System for Cell Preconcentration and Genetic Sample Preparation", *Biomedical Microdevices*, 5:4,303-310 (2003).

Juncker, et al., "Autonomous Microfluidic Capillary Systems", *Anal. Chem*, vol. 74, pp. 6139-6144 (2002).

Linder, et al., "Reagent-Loaded Cartridges for Valveless and Automated Fluid Delivery in Microfluidic Devices", *Anal Chem.*, vol. 77, No. 1, pp. 64-71 (2005).

Moorthy, et al., "Microfluidic tectonics platform: A colorimetric, disposable botulinum toxin enzyme-linked immunosorbent assay system", *Electrophoresis*, vol. 25, pp. 1705-1713 (2004).

Obeid, et al., "Microfabricated Device for DNA and RNA Amplification by Continuous-Flow Polymerase Chain Reaction and Reverse Transcription-Polymerase Chain Reaction with Cycle Number Selection", *Anal. Chem.*, vol. 75, pp. 288-295 (2003).

Proceedings of uTAS 2004, 8th International Conference on Miniaturized Systems in Chemistry and Life Sciences, Sep. 26-30, Malmo, Sweden, Edited by Thomas Laurell, Johan Nilsson, Klays Jensen, D. Jed Harrison, Jorg P. Kutter, The Royal Society of Chemistry, pp. 1-135 (2004).

Sia, S., et al., "An Integrated Approach to a Portable and Low-Cost Immunoassay for Resource-Poor Settings", *Angew. Chem. Int. Ed.*, vol. 43, pp. 498-502 (2004).

Sia, S., et al., "Microfluidic devices fabricated in poly(dimethylsiloxane) for biological studies", Electrophoresis, vol. 24, pp. 3563-3576 (2003).

Song et al., "A microfluidic system for controlling reaction networks in time", *Angew. Chem. Int. Ed.*, vol. 42, No. 7, 768-772 (2003).

Weigle, et al., "Lab-on-a-chip for drug development", *Advanced Drug Delivery Reviews*, vol. 55, pp. 349-377 (2003).

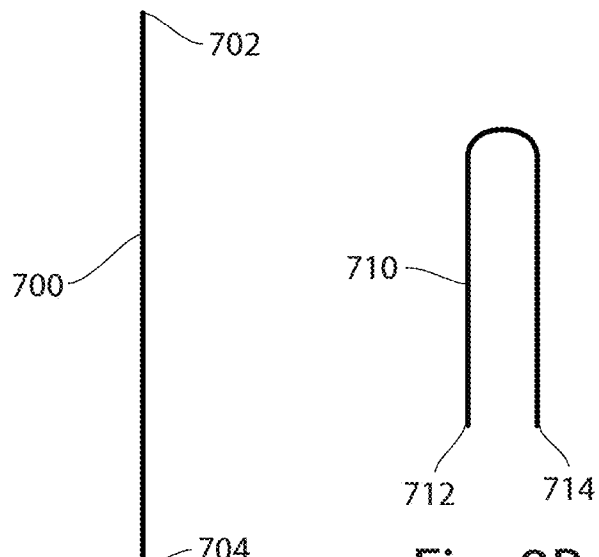
Fig. 8A
Fig. 8B
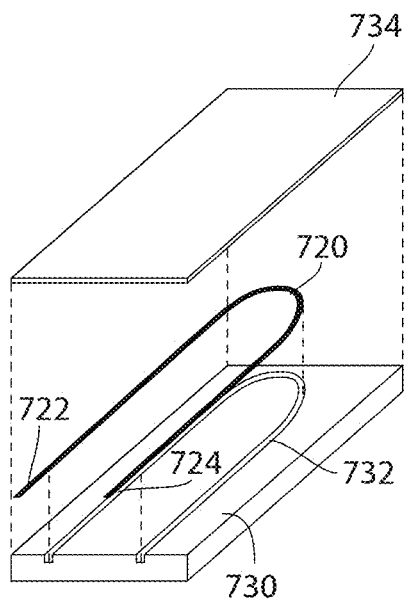
Fig. 8C
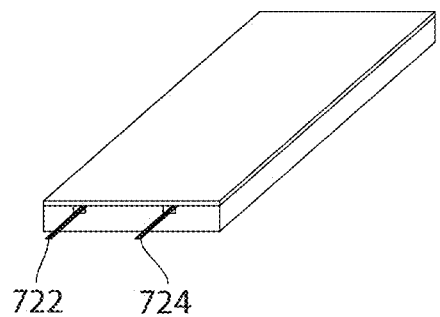
Fig. 8D

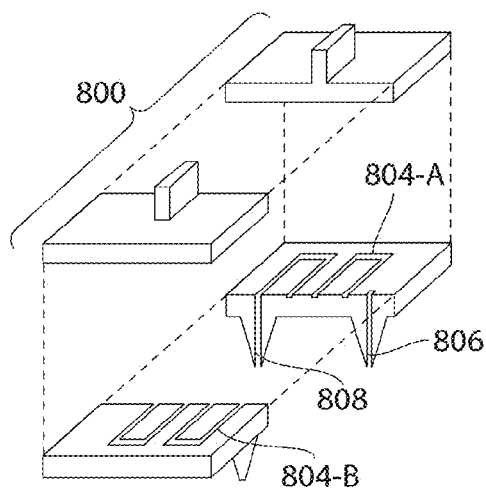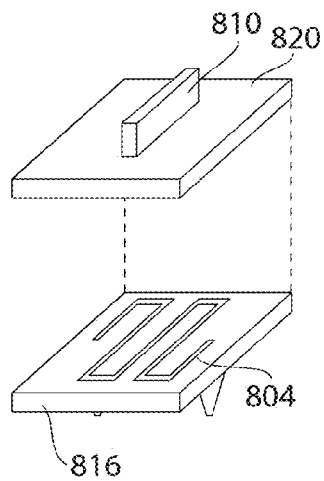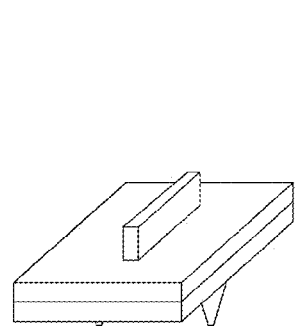
Fig. 9A  Fig. 9B  Fig. 9C
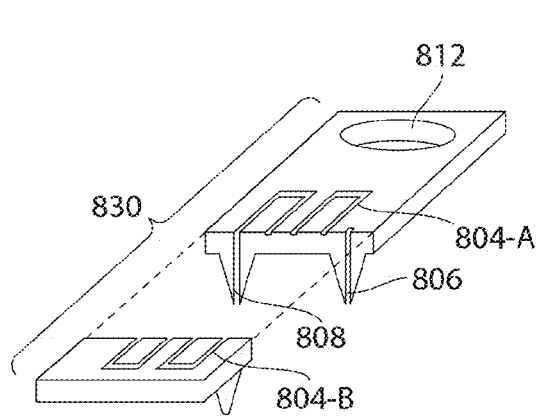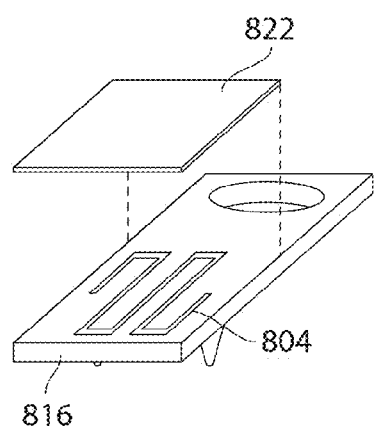
Fig. 9D  Fig. 9E
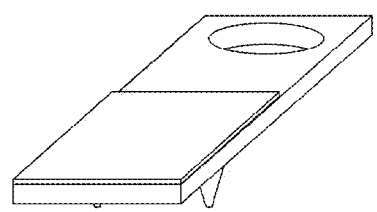
Fig. 9F

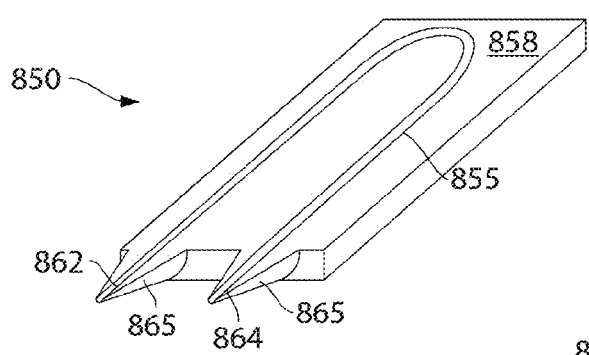
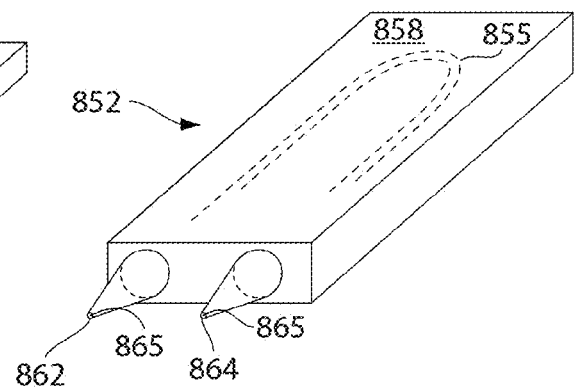
Fig 10A  Fig 10B
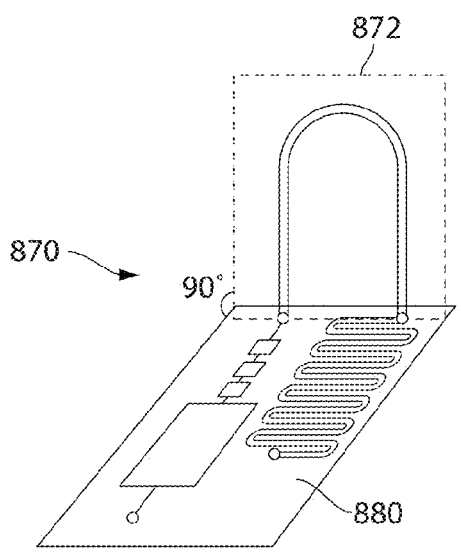
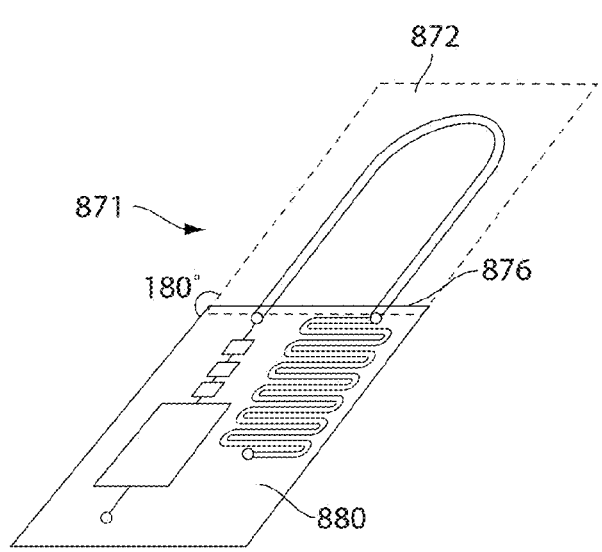
Fig 11A  Fig 11B

FLUIDIC CONNECTORS AND MICROFLUIDIC SYSTEMS

RELATED APPLICATIONS

This application is a continuation of U.S. patent application Ser. No. 14/222,125, filed Mar. 21, 2014, and entitled "Fluidic Connectors and Microfluidic Systems," which is a continuation of U.S. patent application Ser. No. 13/765,042, filed Feb. 12, 2013, and issued as U.S. Pat. No. 8,802,445, and entitled "Fluidic Connectors and Microfluidic Systems", which is a divisional of U.S. patent application Ser. No. 13/467,653, filed May 9, 2012, and issued as U.S. Pat. No. 8,409,527, and entitled "Fluidic Connectors and Microfluidic Systems", which is a continuation of U.S. patent application Ser. No. 12/113,503, filed May 1, 2008 and issued as U.S. Pat. No. 8,202,492, and entitled "Fluidic Connectors and Microfluidic Systems", which claims priority under 35 U.S.C. §119 (e) to U.S. Provisional Patent Application No. 60/927,640, filed May 4, 2007, and entitled "Fluidic Connectors and Microfluidic Systems", each of which is incorporated herein by reference.

FIELD OF INVENTION

The present invention relates generally to microfluidic systems and components thereof, and more specifically, to fluidic connectors, methods, and devices for performing analyses in microfluidic systems.

BACKGROUND

The delivery of fluids plays an important role in fields such as chemistry, microbiology and biochemistry. These fluids may include liquids or gases and may provide reagents, solvents, reactants, or rinses to chemical or biological processes. While various microfluidic devices and methods, such as microfluidic assays, can provide inexpensive, sensitive and accurate analytical platforms, fluid delivery to the platform can add a level of cost and sophistication, as the operation of microfluidic devices often requires the ability to exchange fluids between the device itself and the outside world. In some cases, the operation of the device includes one or a combination of the following: introduction of a sample, introduction of reagents, extraction of a fluid for off-chip analysis or transfer of fluids from one chip to the next.

Because microfluidic devices benefit from scaling law, most applications require only minute quantities of fluid to carry out assays, compared to their bench-top counterparts. Along with the development of these miniaturized systems, the microfluidic community has invested many efforts in designing interfaces between the microfluidic device and the laboratory world. The major problem associated with world-to-chip connection is the mismatch between the volumes used on-chip (e.g., femtoliters to microliters) with respect to the volumes typically handled at the bench (e.g., microliters to liters). For instance, many world-to-chip connectors have dead volume, e.g., wasted volume that may lie at the core of the connector itself. For example, in the case of a tubing with a small inner diameter (e.g., 200 µm to inject small quantities of fluid) connecting to a microchannel (e.g., 10-200 µm in diameter), there may remain a gap between the edge of the tubing and the entrance of the microchannel. The volume defined by that gap is referred to as dead volume, and, in some instances, can be of the same order of magnitude as the total volume of sample to be analyzed. In practice, the dead volume of many devices can often be higher than the volume of sample analyzed by the chip; this is an undesired effect for applications that rely on small sample/reagent consumption.

Accordingly, advances in the field that could, for example, reduce the dead volume and/or allow easy interface between the microfluidic system and the user would be beneficial.

SUMMARY OF THE INVENTION

Fluidic connectors, methods, and devices for performing analyses (e.g., immunoassays) in microfluidic systems are provided.

In one aspect of the invention, a series of devices are provided. In one embodiment, a device includes a microfluidic system formed in a substrate comprising a first microfluidic channel including at least one inlet and one outlet and a second microfluidic channel including at least one inlet and one outlet. The device also includes a fluidic connector that can be connected to the substrate. The fluid connector comprises a fluid path including a fluid path inlet and a fluid path outlet, wherein upon connection, the fluid path inlet connects to the outlet of the first microfluidic channel to allow fluid communication between the fluid path and the first microfluidic channel, and the fluid path outlet connects to the inlet of the second microfluidic channel to allow fluid communication between the fluid path and the second microfluidic channel. The fluid path may contain a reagent (e.g., one or more fluids such as a sample or a series of reagents) disposed therein prior to connection of the fluidic connector to the substrate. In some cases, the microfluidic system is constructed and arranged to operate without recirculation of a fluid in the system.

In some embodiments, the first and second microfluidic channels are not in fluid communication with one another prior to first use, and at first use, the first and second microfluidic channels are brought into fluid communication with one another.

The first microfluidic channel may comprise a first reagent disposed therein prior to connection of the fluidic connector to the substrate. The first microfluidic channel may further comprise a second reagent disposed therein prior to connection of the fluidic connector to the substrate. The first and second reagents may be fluid reagents separated by a fluid immiscible with said first and second reagents. The first and second reagents may be, for example, liquid reagents and the fluid immiscible with said first and second reagents may be a gas. In some embodiments, the second microfluidic channel contains a reagent disposed therein. The reagent in the second microfluidic channel may be dried prior to first use, and, in some cases, is adsorbed to a surface of the second microfluidic channel. The device may further comprises a cover (e.g., a tape) positioned adjacent the substrate so as to enclose the first and second microfluidic channels.

In some embodiments, the device further comprising a reaction area in fluid communication with the first and/or second microfluidic channels, wherein the reaction area allows detection of a chemical and/or biological reaction in the reaction area. The reaction area may comprise at least one meandering channel region. In some cases, the reaction area comprises at least two meandering channel regions connected in series. The at least two meandering channel regions can comprises a chemical and/or biological species that can undergo a chemical and/or biological reaction. Each of the at least two meandering channel regions may allow formation and/or detection of a single, homogenous signal in each of said regions upon carrying out a chemical and/or biological reaction in said regions.

The device may further comprising a first detector aligned with the first meandering channel region. In some embodiments, the device comprises a second detector aligned with the second meandering channel region.

The microfluidic system may include any suitable numbers of channel intersections; for example, the system may include less than 2 channel intersections. In one embodiment, the microfluidic system does not include any channel intersections.

In certain embodiments, the fluid path has a first volume and further comprises a volume control element that can allow introduction of a controlled volume of fluid less than the first volume into the fluid path prior to connection of the fluidic connector to the microfluidic system. The fluidic connector may comprise at least one non-fluidic feature complementary to a feature of the substrate so as to form a non-fluidic connection between the fluidic connector and the substrate upon connection. The fluidic connector may comprise at least one feature complementary to a feature of the substrate so as to form an irreversible connection between the fluidic connector and the substrate. The fluidic connector can further comprise a sampling element that can receive a fluid sample from a biological entity. The fluidic connector may allow transfer of fluid from the biological entity to the fluid path.

In some cases, the device further comprises a source of vacuum that can be connected to an outlet.

In another embodiment, a device comprises a microfluidic system formed in a substrate comprising a first microfluidic channel including an inlet and an outlet and a second microfluidic channel including an inlet and an outlet. The device also includes a fluidic connector that can be connected to the substrate comprising a fluid path including a fluid path inlet and a fluid path outlet, wherein upon connection, the fluid path inlet connects to the outlet of the first microfluidic channel and the fluid path outlet connects to the inlet of the second microfluidic channel. The fluidic connector further comprises at least one non-fluidic feature complementary to a feature of the substrate so as to form a non-fluidic connection between the fluidic connector and the substrate upon connection.

In some cases, the microfluidic system is constructed and arranged to operate without recirculation of a fluid in the system. In some embodiments, the first and second microfluidic channels are not in fluid communication with one another prior to first use, and at first use, the first and second microfluidic channels are brought into fluid communication with one another.

In another embodiment, a device comprises a first microfluidic channel formed in a substrate and containing a first reagent disposed therein, and a second microfluidic channel formed in the substrate and containing a second reagent disposed therein, wherein the first and second microfluidic channels are not in fluid communication with one another prior to first use, and at first use, the first and second microfluidic channels are brought into fluid communication with one another. The first microfluidic channel may further comprise a third reagent, the first and third reagents being separated by a fluid immiscible with said reagents. The second reagent is dried prior to first use.

In another embodiment, a device comprises a microfluidic system formed in a substrate comprising a first microfluidic channel including an inlet and an outlet and a second microfluidic channel including an inlet and an outlet. The device also includes a fluidic connector that can be connected to the substrate and may comprise a fluid path including a fluid path inlet and a fluid path outlet, wherein upon connection, the fluid path inlet connects to the outlet of the first microfluidic channel to allow fluid communication between the fluid path and the first microfluidic channel, and the fluid path outlet connects to the inlet of the second microfluidic channel to allow fluid communication between the fluid path and the second microfluidic channel. The fluid path further comprises a volume control element that can allow introduction of a controlled volume of fluid less than the first volume into the fluid path prior to connection of the fluidic connector to the microfluidic system. In some cases, the volume control element is a frit.

In another embodiment, a device comprises a microfluidic system formed in a substrate comprising a first microfluidic channel including an inlet and an outlet and a second microfluidic channel including an inlet and an outlet. The device also includes a fluidic connector that can be connected to the substrate and may comprise a fluid path including a fluid path inlet and a fluid path outlet, wherein upon connection, the fluid path inlet connects to the outlet of the first microfluidic channel and the fluid path outlet connects to the inlet of the second microfluidic channel. The fluidic connector further comprises a sampling element that can puncture a biological component. The biological component may be human skin. The sampling element may be used to receive a fluid sample from the biological component. The fluidic connector may allow transfer of fluid from the biological entity to the fluid path.

In another aspect of the invention, a series of methods is provided. In one embodiment, a method of storing reagents comprises positioning a first reagent in a first microfluidic channel formed in a substrate and positioning a second reagent in a second microfluidic channel formed in the substrate, wherein the first and second microfluidic channels are not in fluid communication with one another during the positioning steps. The method also includes sealing an inlet and/or outlet of the first microfluidic channel so as to store the first reagent in the first microfluidic channel, and sealing an the inlet and/or outlet of the second microfluidic channel so as to store the second reagent in the second microfluidic channel.

In some embodiments, prior to sealing, the first microfluidic channel contains a third reagent disposed therein, the first and third reagents separated by a fluid immiscible with said reagents. The second reagent may be dried prior to sealing of the inlet of the second microfluidic channel.

In another embodiment, a method comprises providing a first microfluidic channel formed in a substrate and containing a first reagent disposed therein prior to first use, and providing a second microfluidic channel formed in the substrate and containing a second reagent disposed therein prior to first use. The first and second microfluidic channels are not in fluid communication with one another prior to first use, and wherein at first use, the first and second microfluidic channels are brought into fluid communication with one another. The method also includes causing the first and second microfluidic channels to be in fluid communication with one another.

In some embodiments, the causing step comprises connecting a fluid path between the first and second microfluidic channels. The fluid path may contains a sample disposed therein. The sample may be, for example, a fluid sample.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 8A-8D are schematic diagrams of an open-ended fluidic device and fluidic connectors according to an embodiment of the invention;

FIGS. 9A-9F are schematic diagrams of monolithic fluidic connectors according to an embodiment of the invention;

FIGS. 10A and 10B are schematic diagrams of another fluidic connector according to an embodiment of the invention;

FIGS. 11A and 11B are schematic diagrams of fluidic connectors that can be connected orthogonally or on the same plane as the channels of a microfluidic system according to an embodiment of the invention;

DETAILED DESCRIPTION

Fluidic connectors, methods, and devices for performing analyses (e.g., immunoassays) in microfluidic systems are provided. In some embodiments, a fluidic connector having a fluid path is used to connect two independent channels formed in a substrate so as to allow fluid communication between the two independent channels. One or both of the independent channels may be pre-filled with reagents (e.g., antibody solutions, washing buffers and amplification reagents), which can be used to perform the analysis. These reagents may be stored in the channels of the substrate for long periods amounts of time (e.g., 1 year) prior to use. Prior to connection of the fluid connector and the substrate, the fluid path may be filled with a sample (e.g., blood). The sample may be obtained, for example, by pricking a finger of a user until blood is drawn from the finger into the fluid path (e.g., by capillary forces). Upon connection of the fluidic connector and the channels of the substrate, the sample can pass through a reaction area within the first channel of the substrate. This process can allow components of the sample to interact with components disposed in the reaction area. Afterwards, reagents from the second channel can flow to the reaction area via the fluid path, allowing components in the reaction area to be processed (e.g., amplified to produce detectable signal). Components in the reaction area can then be determined using various methods of detection.

Microfluidic systems described herein may be useful for performing chemical and/or biological reactions, especially immunoassays, with one or more advantages such as: (a) use of small amounts of sample with little or no sample waste, (b) long-term stability of chemical and/or biological reagents stored in the device, (c) reduction of cross-contamination between stored reagents and/or between sample and reagent, (d) sample metering, (e) ease of use to untrained users for introducing a sample into the device, (f) efficient mixing of reagents, and (g) assay reliability. These and other advantages are described in more detail below in connection with the description and figures.

The articles, systems, and methods described herein may be combined with those described in International Patent Publication No. WO2005/066613 (International Patent Application Serial No. PCT/US2004/043585), filed Dec. 20, 2004 and entitled "Assay Device and Method," International Patent Publication No. WO2005/072858 (International Patent Application Serial No. PCT/US2005/003514), filed Jan. 26, 2005 and entitled "Fluid Delivery System and Method," and International Patent Publication No. WO2006/113727 (International Patent Application Serial No. PCT/US06/14583), filed Apr. 19, 2006 and entitled "Fluidic Structures Including Meandering and Wide Channels," each of which is incorporated herein by reference in its entirety.

Figure 1A:
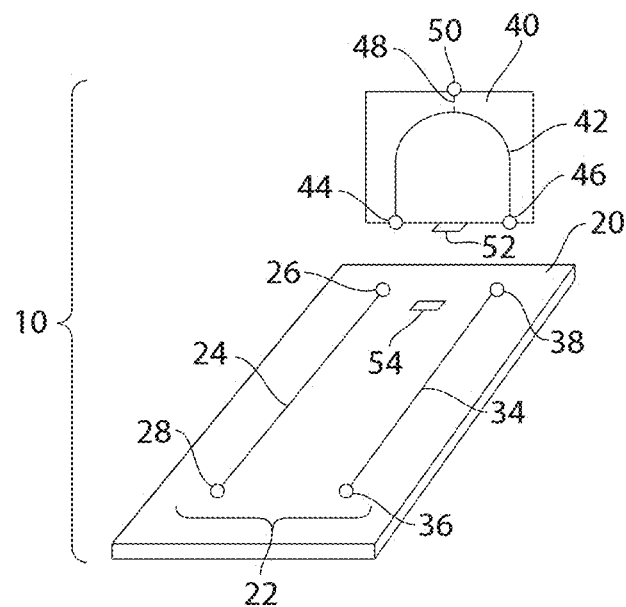
FIGS. 1A and 1B are schematic diagrams of a microfluidic device including a fluidic connector according to an embodiment of the invention.

FIG. 1 shows a microfluidic device 10 according to one embodiment of the invention. As shown in this illustrative embodiment, device 10 comprises two attachable units: substrate 20, which includes a microfluidic system 22, and a fluidic connector 40, which can be used to connect two independent microfluidic channels of the substrate. Microfluidic system 22 of substrate 20 includes channel 24 having an inlet 26 and an outlet 28, as well as channel 34 having an inlet 36 and an outlet 38. As shown in the illustrative embodiment of FIG. 1A, channels 24 and 34 are not connected; that is, there is no fluid communication between the channels. As described in more detail below, non-connected channels may be advantageous in certain cases, such as for storing different reagents in each of the channels. For example, channel 24 may be used to store dry reagents and channel 34 may be used to store wet reagents. Having the channels be physically separated from one another can enhance long-term stability of the reagents stored in each of the channels, e.g., by keeping the reagent(s) stored in dry form protected from moisture that may be produced by reagent(s) stored in wet form.

As shown, fluidic connector 40 includes a fluid path 42 having an inlet 46 and an outlet 44. Fluidic connector 40 can be connected to substrate 20, e.g., via the inlets and outlets. Upon connection, fluid path inlet 46 connects to outlet 38 of microfluidic channel 34 and fluid path outlet 44 connects to inlet 26 of microfluidic channel 24. This connection causes fluid communication between channels 24 and 34 via fluid path 42. The connections between the inlets and outlets of the article and the substrate may form fluid-tight seals to prevent leakage at the points of connection. Accordingly, as illustrated in FIG. 1B, if fluid flows in the direction of arrow 56, at least a portion of a fluid in channel 34 can flow into fluid path 42 and then into channel 24, optionally exiting at outlet 28.

Although FIG. 1A shows only two separate channels forming microfluidic system 22, in other embodiments, a microfluidic system may include more than two separate channels, and a fluidic connector can be used to connect three or more such channels of a substrate. In such embodiments, a fluidic connector may have multiple fluid paths (which may be interconnected or independent) and/or multiple inlets and/or outlets that can connect to several different microfluidic channels of the substrate. Additionally, although FIG. 1 shows two separate channels 24 and 34 on the same substrate, article 40 can be used to connect channels on different substrates.

Figure 1B:
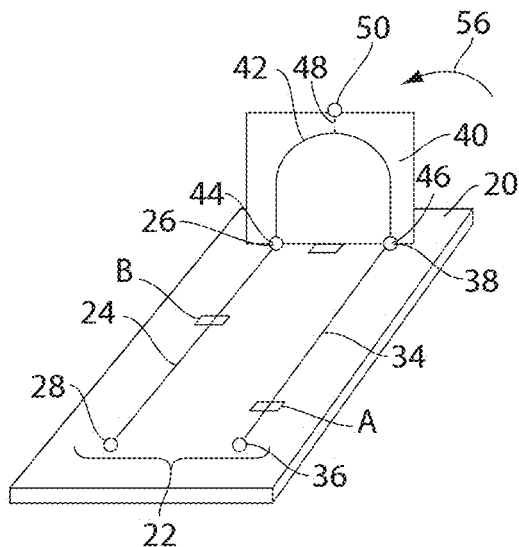

The microfluidic system formed by the connection of two independent channels of a substrate using a fluidic connector, as shown in FIG. 1B, is an example of an "open-loop" system. As used herein, an "open-loop" system is constructed and arranged to operate without recirculation of a fluid within the microfluidic system. In other words, a fluid portion starting out at a first position within the microfluidic system does not pass the first position again after it leaves that position. Instead, the fluid portion may exit the device at an outlet (unless, for example, the fluid portion gets processed or used up in the microfluidic system). For example, as illustrated in FIG. 1B, a fluid portion initially at position "A" and flowing in the direction of arrow 56 may flow into fluid path 42 and then into channel 24, optionally exiting at outlet 28; however, the design of the microfluidic system does not allow the fluid portion to re-enter channel 34 and to pass though position "A" again. Similarly, a fluid portion initially at position "B" and flowing in the direction of arrow 56 may exit outlet 28; this fluid portion cannot enter into channel 34 or 24 to allow the portion to pass though position "B" again. In some cases, the microfluidic system does not allow recirculation of a fluid within the system (e.g., during intended use).

In other embodiments, a fluidic connector can be used to form a "closed-loop" system. As used herein, a "closed-loop" system may allow recirculation of a fluid within the microfluidic system such that a fluid portion starting out at a first position within the microfluidic system can pass the first position again after it leaves that position. For example, if a second fluidic connector (e.g., one similar to fluidic connector 40) was used to connect inlet 36 and outlet 28 of substrate 20 of FIG. 1B, a closed-loop system would be formed. Alternatively, if microfluidic system 22 was designed so that inlet 36 and outlet 28 were joined such that channels 24 and 34 formed a single continuous channel, the connection of fluidic connector 40 to inlet 38 and outlet 26 would form a closed-loop system.

It should also be understood that a device described herein may include more than one fluidic connector. Multiple fluid connectors are useful for connecting multiple channels (or portions of channels) of one or more substrates.

In certain embodiments, a fluidic connector may be used to connect two (or more) portions of a single microfluidic channel of a substrate. It should be understood that where at least first and second separate (independent) channels of a substrate are described herein, a fluidic connector may be used to connect similar embodiments but where at least a portion of the first channel is in fluid communication with at least a portion of the second channel (e.g., to form a single interconnected channel) prior to connection using the fluidic connector.

Optionally, and as described in more detail below, fluidic connector 40 may include at least one non-fluidic feature 52 complementary to a feature 54 of the substrate so as to form a non-fluidic connection between the fluidic connector and the substrate upon connection of the fluid path. This non-fluidic connection can help to stabilize the connection between the fluidic connector and substrate.

In some embodiments, fluidic connector 40 can be used to introduce one or more fluids (e.g., a sample such as blood, serum, plasma, tear fluid, saliva, urine, sperm, sputum, or any other fluid of interest such as a buffer) into the microfluidic system of substrate 20. This can allow the sample (or other fluid) to bypass at least one channel of the substrate. For example, if a sample is first introduced into fluid path 42 and then fluidic connector 40 is connected to substrate 20 as shown in FIG. 1B, flow of the fluids in the direction of arrow 56 allows the sample contained in fluid path 42 to flow into channel 24, but not channel 34. Such a design may be useful for cases in which the sample to be delivered via fluid path 42 contaminates or otherwise undesirably affects one or more components within channel 34. It should be understood, however, that the fluidic connector need not be used to introduce fluids into the device, but can be used, in some embodiments, simply to fluidly connect at least two channels of a device or devices.

As described above, a fluid may be introduced into fluid path 42 via inlet 46 (or outlet 44, which may act as an inlet for purposes of fluid introduction). All or a portion of fluid path 42 may be filled with the fluid. Optionally, fluidic connector 40 may include a secondary flow path 48, which connects inlet 50 to flow path 42. This design can allow, for example, the introduction of a fluid into fluid flow path 42 via inlet 50 and secondary path 48 before or after the fluidic connector has been connected to the substrate (e.g., as shown in FIG. 1B). Alternatively, a fluid can be introduced into fluid path 42 via inlet 50 prior to connection of the fluidic connector and the substrate. In some embodiments, inlet 50 and secondary fluid path 48 can be blocked (e.g., with a plunger or using any other suitable method) after introducing fluid into fluid path 42 via inlet 50 and secondary fluid path 48. This blocking can decrease the number of channel intersections of the microfluidic system during operation of the device, and may be advantageous for reasons described below.

In some embodiments, microfluidic systems described herein (including device substrates and fluidic connectors) contain stored reagents prior to first use of the device and/or prior to introduction of a sample into the device. The use of stored reagents can simplify use of the microfluidic system by a user, since this minimizes the number of steps the user has to perform in order to operate the device. This simplicity can allows microfluidic systems described herein to be used by untrained users, such as those in point-of-care settings. Stored reagents in microfluidic devices are particularly useful for devices designed to perform immunoassays.

Figure 2:
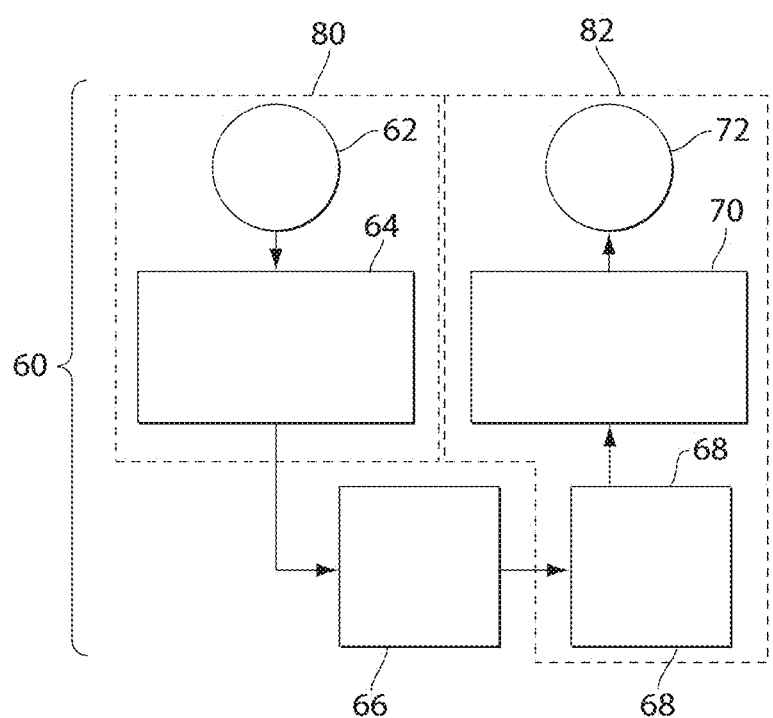
FIG. 2 is a block diagram of a microfluidic system that may contain stored reagents and can be used for performing an a chemical and/or biological reaction according to an embodiment of the invention.

FIG. 2 shows a block diagram 60 of a microfluidic device that may contain stored reagents and can be used for performing an a chemical and/or biological reaction (e.g., an immunoassay). The microfluidic device includes a reagent inlet 62 in fluid communication with a reagent storage area 64, which may include, for example, one or more channels and/or reservoirs. The device may also include a sample loading area 66, such as a fluidic connector that can connect reagent storage area 64 to reaction area 68. The reaction area, which may include one or more areas for detecting a component in a sample (e.g., detection zones), may be in fluid communication with waste area 70 and coupled to outlet 72. In some embodiments, reaction area 68 is an immunoassay area.

In the exemplary embodiment shown in FIG. 2, section 80 comprises the reagent inlet and reagent storage area, and section 82 comprises the reaction area, waste area, and outlet. Reagents may be stored in one or both of sections 80 and 82. For example, in one particular embodiment, a reagent is stored in the form of a fluid (e.g., a liquid or a gas) in reagent storage area 64 of section 80, and a reagent in the form of a dry film is stored in reaction area 68 of section 82.

In some embodiments, sections 80 and 82 are in fluid communication with one another (e.g., via sample loading area 66) prior to introduction of a sample into the device. For example, if sample loading area 66 included fluidic connector 40 of FIG. 1, the fluidic connector can be connected to the substrate to cause fluid communication between sections 80 and 82. Subsequently, a sample may be introduced into the device via inlet 50 and secondary fluid path 48.

In other embodiments, sections 80 and 82 are not in fluid communication with one another prior to introduction of a sample into the device. For example, if sample loading area 66 included fluidic connector 40 of FIG. 1 which did not have inlet 50 or secondary fluid path 48, the fluidic connector may first be filled with a sample and then connected to the substrate to cause fluid communication between sections 80 and 82. In this example, the sample is introduced into the channels of the substrate at the time when (or shortly after) fluid communication is formed between sections 80 and 82. In such instances, sections 80 and 82 are not in fluid communication with one another prior to first use of the device, wherein at first use, the sections are brought into fluid communication with one another.

As described herein, one or more reagents that may be used in a chemical and/or biological reaction may be stored and/or disposed in the device (e.g., in a device substrate and/or a fluid connector) prior to first use and/or prior to introduction of a sample into the device. Such reagents may be stored and/or disposed in fluid and/or dry form, and the method of storage/disposal may depend on the particular application. Reagents can be stored and/or disposed, for example, as a liquid, a gas, a gel, a plurality of particles, or a film. The reagents may be positioned in any suitable portion of a device, including, but not limited to, in a channel, reservoir, on a surface, and in or on a membrane, which may optionally be part of a reagent storage area. A reagent may be associated with a microfluidic system (or components of a system) in any suitable manner. For example, reagents may be crosslinked (e.g., covalently or ionically), absorbed, or adsorbed (physisorbed) onto a surface within the microfluidic system. In one particular embodiment, all or a portion of a channel (such as a fluid path of a fluid connector or a channel of the device substrate) is coated with an anti-coagulant (e.g., heparin). In some cases, a liquid is contained within a channel or reservoir of a device prior to first use and/or prior to introduction of a sample into the device.

In some embodiments, dry reagents are stored in one section of a microfluidic device and wet reagents are stored in a second section of a microfluidic device. Alternatively, two separate sections of a device may both contain dry reagents and/or wet reagents. The first and second sections may be in fluid communication with one another prior to first use, and/or prior to introduction of a sample into the device, in some instances. In other cases, the sections are not in fluid communication with one another prior to first use and/or prior to introduction of a sample into the device. During first use, a stored reagent may pass from one section to another section of the device. For instance, a reagent stored in the form of a fluid can pass from a first section to a second section of the device after the first and second sections are connected via a fluid path (e.g., a fluidic connector). In other cases, a reagent stored as a dried substance is hydrated with a fluid, and then passes from the first section to the second section upon connection of the sections. In yet other cases, a reagent stored as a dried substance is hydrated with fluid, but does not pass from one section to another section upon connection of the sections. Methods of storing reagents are described in further detail below.

It should be understood that while the microfluidic system presented by block diagram 60 includes only two sections 80 and 82, a microfluidic device may include additional sections in other embodiments. Additionally, the sequence of fluid flow between reagent storage area 64, sample loading area 66, and reaction area 68 may be different in some devices. For example, fluid flow may be directed from a reagent storage area to reaction area followed by fluid flow from a sample loading area to the reaction area. Other arrangements are also possible.

FIGS. 3A-3D show an example of a microfluidic device including a fluidic connector and containing stored reagents that can be used in a chemical and/or biological reaction. Device 100 includes a first section 106 including reagent storage area 110, which is in the form of a channel 112 and includes an inlet 116 and an outlet 118. Different reagents may be stored in channel 112 depending on the particular application. For example, if the device were used to perform an immunoassay, the channel may have stored therein, in series, a rinse fluid 120, an antibody fluid 122, a rinse fluid 124, a labeled-antibody fluid 126, and a rinse fluid 128. Additional reagents and rinse fluids may also present as needed. These reagents may be in the form of plugs (e.g., liquid plugs) that are separated from one another by immiscible fluid plugs 130 (e.g., a separation fluid such as a gas (e.g., air, nitrogen, or argon) or an oil (e.g., a fluorocarbon or hydrocarbon)). In FIG.

3A, inlet 116 and outlet 118 are sealed so as to prevent evaporation and contamination of the stored reagents.

Device 100 also includes a second section 150 having an inlet 154, an outlet 156, a channel 158, reaction area 160, and a waste area 174. The reaction area may include several detection zones 162, 164, 166, and 168. The detection zones may have any suitable configuration and/or arrangement. In one embodiment, each of the detection zones is in the form of a meandering (serpentine) channel, as described in more detail below and in International Patent Publication No. WO2006/113727 (International Patent Application Serial No. PCT/US06/14583), filed Apr. 19, 2006 and entitled "Fluidic Structures Including Meandering and Wide Channels," which is incorporated herein by reference in its entirety. The detection zones may be arranged to detect, for example, different components of sample, or may be used as positive and/or negative controls. In some cases, one or more of the detection zones contains a reagent stored therein. In one particular embodiment, a device used for performing an immunoassay includes a series of stored dry reagents. The reagents may be physisorbed onto a surface of the meandering channel. For example, detection zone 162 may include a negative control (e.g., a detergent known to prevent adhesion of proteins), detection zones 164 and 166 may include different concentrations of antibodies that may bind to a component in a sample (or two different antibodies that can bind to different components in the sample), and detection zone 168 may include a positive control (e.g., the same antigen expected to be determined from a sample). The positive control may be used as a qualitative control; for example, if a signal reaches a certain threshold, the test can be considered valid. Additionally and/or alternatively, the positive control can also be as a quantitative tool; for example, the intensity of the signal can be can be part of an on-chip calibration process.

Figure 3A:
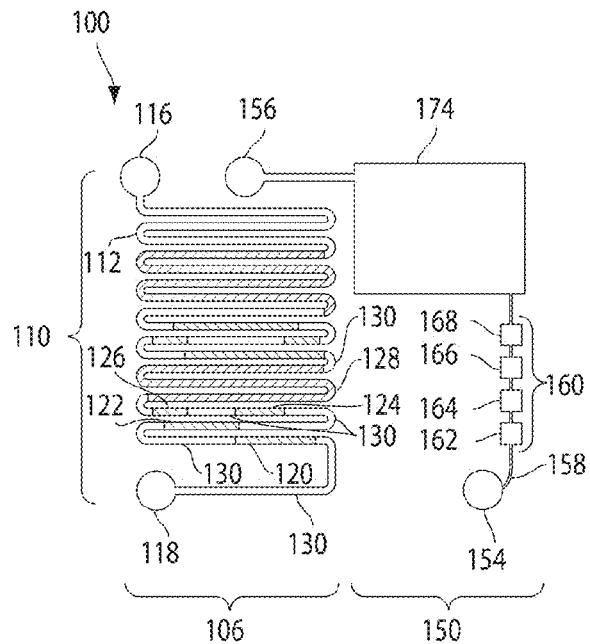
FIGS. 3A-3D are schematic diagrams of a microfluidic device including a fluidic connector and containing stored reagents used to perform a chemical and/or biological reaction according to an embodiment of the invention.

As shown in the embodiment illustrated in FIG. 3A, each of the areas within section 150 are in fluid communication with one another, but none are in fluid communication with any of the components of section 106. In certain embodiments, section 150 containing stored dry reagents and section 106 containing stored wet reagents are configured to not be in fluid communication with one another prior to first use because this configuration can promote long-term storage of each of the reagents in their respective sections, as described further below.

Figure 3B:
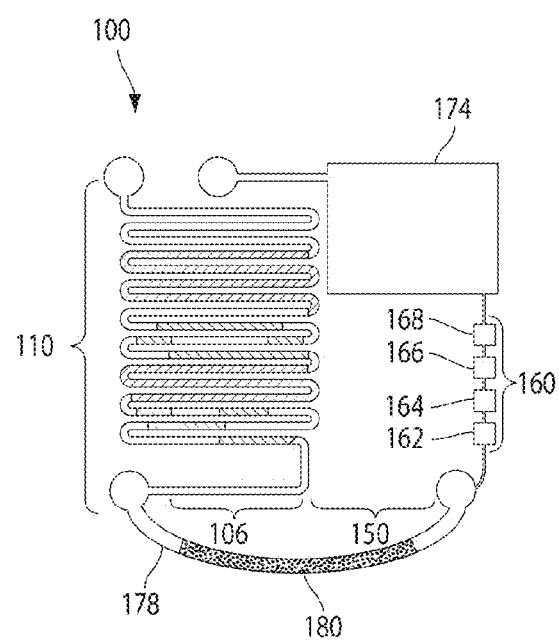

As shown in FIG. 3B, sections 106 and 150 can be connected using fluidic connector 178, causing sections 106 and 150 to be in fluid communication with one another. If outlet 118 and inlet 154 are covered with a seal (e.g., a biocompatible tape) in FIG. 3A, this connection can cause the sealings over the outlet and inlet to be pierced, broken, or removed.

Fluidic connector 178 may be used for sample loading and may include sample 180 contained therein. As described herein, sample 180 may be introduced into fluidic connector 178 by an suitable method, and, in some cases, is introduced into the fluidic connector prior to there being fluid communication between sections 106 and 150.

Figure 3C:
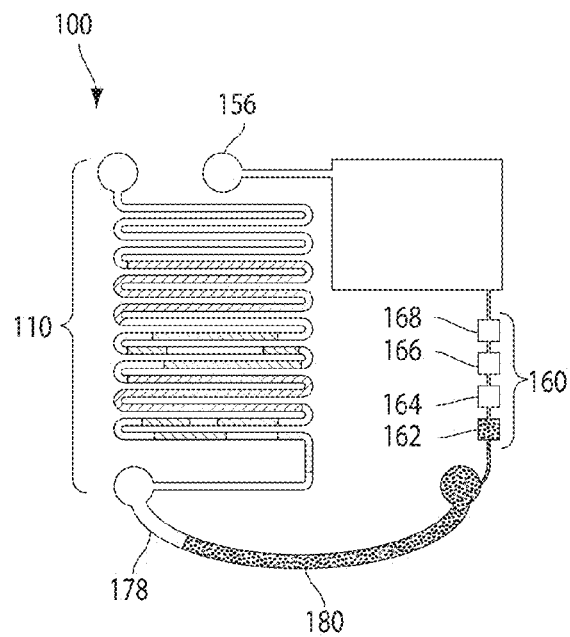

As shown in the embodiment illustrated in FIG. 3C, fluids in reagent storage area 110 and sample 180 may flow from section 106 towards section 150. Fluid flow may take place, for example, by applying a positive pressure to inlet 116 (e.g., using a plunger, gravity, or a pump) or by applying a vacuum source to outlet 156. In such embodiments, a source of positive pressure and/or vacuum may be connected to one or more inlet(s) and/or outlet(s), respectively.

Figure 3D:
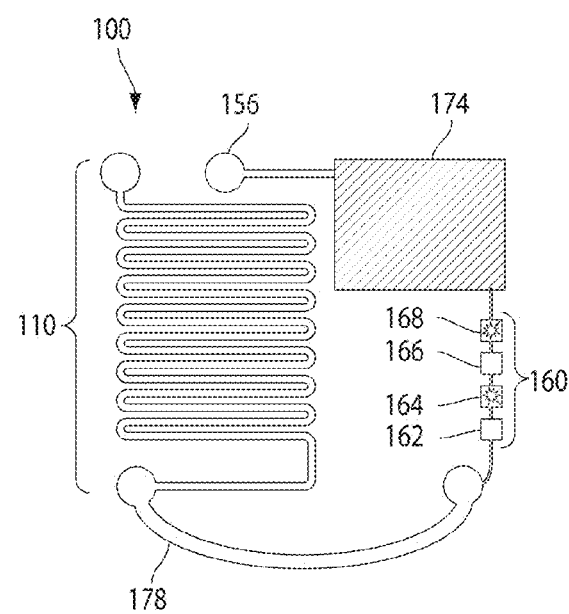

Sample 180 first flows into reaction area 160 (FIG. 3C), and then into waste area 174 (FIG. 3D). The passing of the sample through the detection zones allows interaction (e.g., binding) between one or more components of the sample (e.g., an antigen) and one or more components in the reaction area (e.g., an antibody). As described herein, the component(s) of the reaction area may be in the form of dried reagents stored in the reaction area prior to first use. This interaction may form a product such as a binding pair complex. In some cases, this interaction alone causes a signal to be determined (e.g., measured) by a detector coupled to the microfluidic system. In other cases, in order for an accurate signal to be determined by the detector, the product is treated by one or more reagents from reagent storage area 110. For example, a reagent stored in reagent storage area 110 may be a labeled-antibody that interacts with an antigen of the sample. This interaction can allow the product to be labeled or the signal from the product to be amplified.

In one particular embodiment involving an immunoassay, the stored reagents in the storage area include an enzyme amplification solution and a precipitating dye (e.g., diaminobenzidine, DAB). The one or more reagents from reagent storage area 110 is allowed to pass through each of the detection zones. These reagents may interact further with a binding pair complex, e.g., to amplify the signal and/or to label the complex, as depicted in detection zones 164 and 168 of FIG. 3D.

By maintaining an immiscible fluid (a separation fluid) between each of the reagents in the reagent storage area, the stored fluids can be delivered in sequence from the reagent storage area while avoiding contact between any of the stored fluids. Any immiscible fluid that separates the stored reagents may be applied to the reaction area without altering the conditions of the reaction area. For instance, if antibody-antigen binding has occurred at one of the detection zones of the reaction area, air can be applied to the site with minimal or no effect on any binding that has occurred.

As described herein, storing reagents in a microfluidic system can allow the reagents to be dispensed in a particular order for a downstream process (e.g., amplifying a signal in a reaction area). In cases where a particular time of exposure to a reagent is desired, the amount of each fluid in the microfluidic system may be proportional to the amount of time the reagent is exposed to a downstream reaction area. For example, if the desired exposure time for a first reagent is twice the desired exposure time for a second reagent, the volume of the first reagent in a channel may be twice the volume of the second reagent in the channel. If a constant pressure differential is applied in flowing the reagents from the channel to the reaction area, and if the viscosity of the fluids is the same or similar, the exposure time of each fluid at a specific point, such as a reaction area, may be proportional to the relative volume of the fluid. Factors such as channel geometry, pressure or viscosity can also be altered to change flow rates of specific fluids from the channel.

Additionally, this strategy of storing reagents in sequence, especially amplification reagents, can be adapted to a wide range of chemistries. For example, various amplification chemistries that produce optical signals (e.g., absorbance, fluorescence, glow or flash chemiluminescence, electrochemiluminescence), electrical signals (e.g., resistance or conductivity of metal structures created by an electroless process) or magnetic signals (e.g., magnetic beads) can be used to allow detection of a signal by a detector.

The use of gaseous (e.g., air) plugs to separate reagents requires the overall microfluidic device to be compatible with many air bubbles. Although air bubbles may be stabilized and/or controlled within microfluidic devices using a variety of methods, one particular method used in certain embodiments described herein includes limiting the number of channel intersections in the system. Accordingly, microfluidic devices described herein may be designed to have few (e.g., less than 5, 4, 3, or 2), one, or no channel intersections. As used herein, a channel intersection includes at least three channels (or portions of one or more channels) intersecting at a single point (e.g., forming a "Y"). For example, device 100 of FIG. 3 does not have any channel intersections and device 200 of FIG. 4 has only one channel intersection 219. Devices that do not have any channel intersections may be useful, for example, for performing reactions that do not require mixing of reagents (e.g., stored reagents).

FIGS. 4A-4D show another example of a microfluidic device including a fluidic connector and containing stored reagents that can be used in a chemical and/or biological reaction. As shown in these illustrative embodiments, device 200 includes a first section 202 comprising reagent storage area 204. The reagent storage area has two parts: upper portion 205 and lower portion 206. The upper portion includes channel 208 having inlet 216 connected thereto and channel 209 having inlet 217 connected thereto. Channels 208 and 209 are separated in the upper portion and meet at intersection 219, which is connected to channel 212 of the lower portion. Channel 212 is connected to an outlet 218. Device 200 having two inlets 216 and 217, each connected to a different channel, may be useful, for example, for performing reactions in which two reagents need to be stored separately on the device, but which require mixing during use or immediately before use.

In one particular embodiment, device 200 is used to perform an immunoassay for human IgG, which uses sliver enhancement for signal amplification. A solution of silver salts is stored in channel 208 and a solution of hydroquinone is stored in channel 209. Because these two components, which can produce signal amplification upon mixing, are located in separate channels, they cannot mix with each other until the flow drives both solutions towards intersection 219.

Figure 4A:
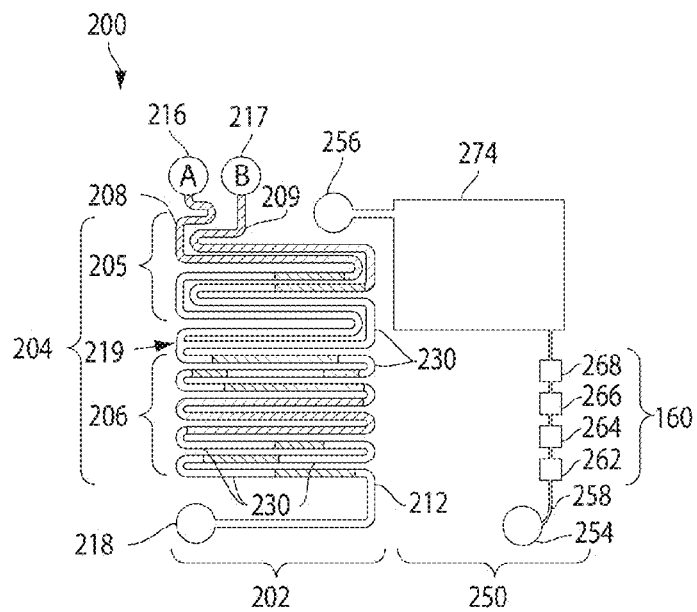
FIGS. 4A-4D are schematic diagrams of a microfluidic device including a fluidic connector and containing stored reagents used to perform a chemical and/or biological reaction according to an embodiment of the invention.

Reagents that do not have to be mixed with one another can be stored in lower portion 206 of the reagent storage area. These reagents can include, for example, rinse fluids, antibody fluids, and other fluids as needed. The reagents may be in the form of plugs that are separated from one another by immiscible fluid plugs 230 (e.g., a separation fluid such as a gas (e.g., air) or an oil). In FIG. 4A, inlets 216 and 217, and outlet 218 are sealed so as to prevent evaporation and contamination of the stored reagents.

Device 200 also includes a second section 250 having an inlet 254, an outlet 256, a channel 258, a reaction area 260, and a waste area 274. The reaction area may include several detection zones 262, 264, 266, and 268. Optionally, one or more detection zones may be in the form of a meandering channel region, as described herein. The detection zones may be arranged to detect, for example, different components of sample, or used as positive and/or negative controls. In some cases, one or more of the detection zones contains a reagent stored therein. In one embodiment, a device used for performing an immunoassay includes a series of stored dry reagents. The reagents may be physisorbed onto a surface of a meandering channel of a detection zone.

In one particular embodiment, wherein device 200 is used for performing an immunoassay for human IgG and uses sliver enhancement for signal amplification, one or more surfaces of the meandering channels of the reaction area is modified by biomolecules such as BSA (bovine serum albumin) or Tween, a negative control (e.g., a detergent known to prevent adhesion of proteins), different concentrations of antibodies (e.g., anti-human IgG) that may bind to a component in a sample, and human IgG, a positive control (e.g., the same antigen expected to be determined from a sample).

These reagents are stored in section 250 prior to use by sealing inlet 254 and outlet 256.

Figure 4B:
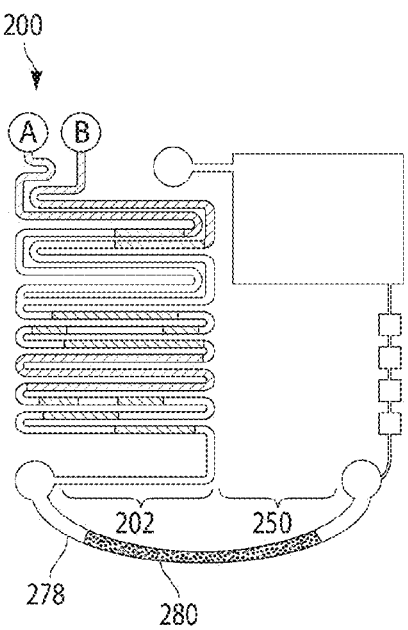

As shown in FIG. 4B, sections 202 and 250 can be connected using fluidic connector 278, causing sections 202 and 250 to be in fluid communication with one another. Fluidic connector 278 may be used for sample loading and may include sample 280 (e.g., blood) contained therein. As described herein, sample 280 may be introduced into fluidic connector 278 by an suitable method, and, in some cases, is introduced into the fluidic connector prior to there being fluid communication between sections 202 and 250.

Figure 4C:
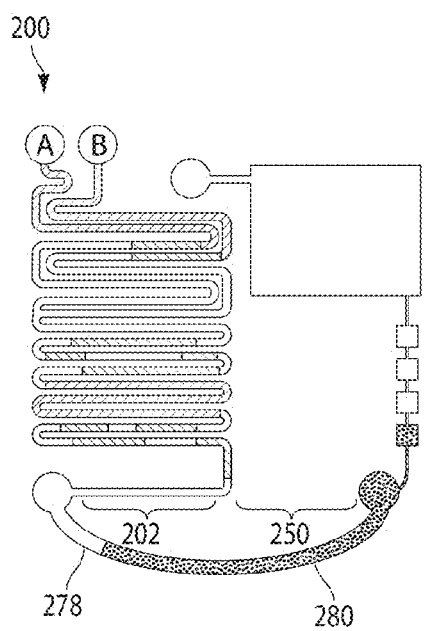
Figure 4D:
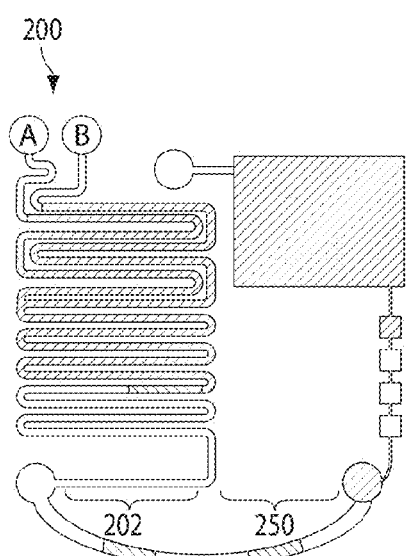

As shown in the embodiment illustrated in FIG. 4C, fluids in reagent storage area 204 and sample 280 may flow towards section 250. Fluid flow may take place, for example, by applying a positive pressure to inlets 216 and 217 (e.g., using a plunger, gravity, or a pump) or by applying a vacuum source to outlet 256. Sample 280 first flows into reaction area 260 (FIG. 4C), and then into waste area 274 (FIG. 4D). The passing of the sample through the detection zones allows interaction (e.g., binding) between one or more components of the sample and one or more components stored in the reaction area. This interactions may form, for example, a product such as a binding pair complex. Subsequent flow of fluids from the reagent storage area over the detection zones can cause labeling of the product and/or signal amplification.

In one particular embodiment, device 200 is used for performing an immunoassay for human IgG and uses sliver enhancement for signal amplification. After delivery of a sample containing human IgG from the fluidic connector to the reaction area, binding between the human IgG and a stored dry reagent, anti-human IgG, can take place. This binding can form a binding pair complex in a detection zone. Stored reagents from lower portion 206 of reagent storage area 204 can then flow over this binding pair complex. One of the stored reagents may include a solution of metal colloid (e.g., a gold conjugated antibody) that specifically binds to the antigen to be detected (e.g., human IgG). This metal colloid can provide a catalytic surface for the deposition of an opaque material, such as a layer of metal (e.g., silver), on a surface of the detection zone. The layer of metal can be formed by using a two component system as described above: a metal precursor (e.g., a solution of silver salts), which can be stored in channel 208, and a reducing agent (e.g., hydroquinone), which can be stored in channel 209. As a positive or negative pressure differential is applied to the system, the silver salt and hydroquinone solutions eventually merge at intersection 219, where they mix slowly (e.g., due to diffusion) along channel 212, and then flow over the reaction area. Therefore, if antibody-antigen binding occurs in the reaction area, the flowing of the metal precursor solution through the area can result in the formation of an opaque layer, such as a silver layer, due to the presence of the catalytic metal colloid associated with the antibody-antigen complex. The opaque layer may include a substance that interferes with the transmittance of light at one or more wavelengths. Any opaque layer that is formed in the microfluidic channel can be detected optically, for example, by measuring a reduction in light transmittance through a portion of the reaction area (e.g., a meandering channel) compared to a portion of an area that does not include the antibody or antigen. Alternatively, a signal can be obtained by measuring the variation of light transmittance as a function of time, as the film is being formed in a detection zone. The opaque layer may provide an increase in assay sensitivity when compared to techniques that do not form an opaque layer.

FIGS. 5A-5F show images of a device used to perform a human IgG immunoassay according to one embodiment of the invention, and is described in more detail in the Examples section.

Although immunoassays are primarily described, it should be understood that devices described herein may be used for any suitable chemical and/or biological reaction, and may include, for example, other solid-phase assays that involve affinity reaction between proteins or other biomolecules (e.g., DNA, RNA, carbohydrates), or non-naturally occurring molecules.

Moreover, although many embodiments described herein include the use of a fluidic connector to connect two channels or two portions of a channel, embodiments herein also include articles and methods for introducing a sample into a microfluidic system without using a fluidic connector. For example, in some embodiments, an open-ended fluidic device (i.e., a device where only one end is connected to a microfluidic system) may be used to introduce a sample into the microfluidic system.

Figure 6:
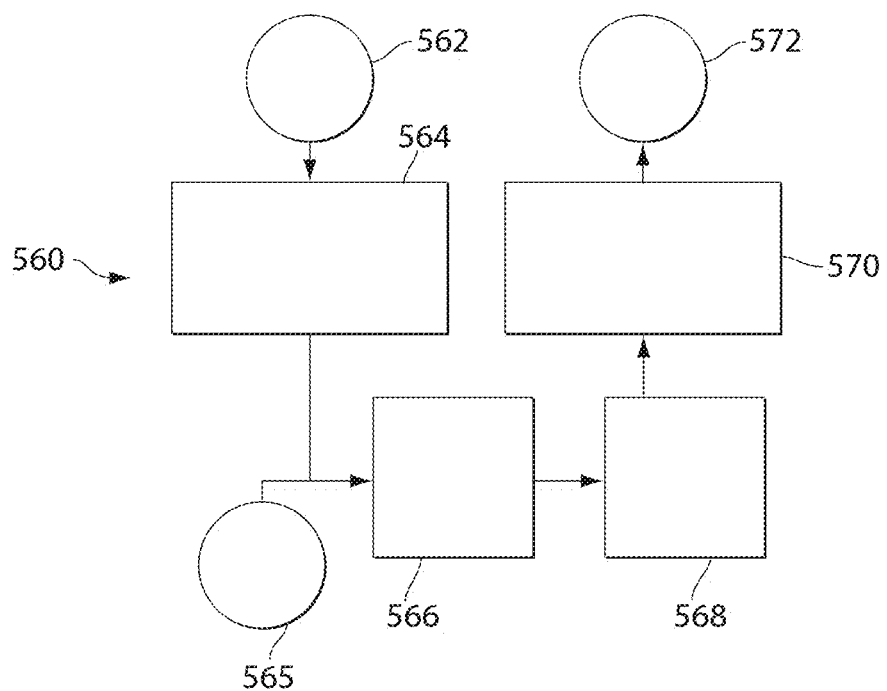
FIG. 6 is a block diagram of a microfluidic system according to an embodiment of the invention.

FIG. 6 shows a block diagram 560 of a microfluidic device that is compatible with using an open-ended device for sample introduction. The microfluidic device may contain stored reagents and can be used for performing an a chemical and/or biological reaction (e.g., an immunoassay). The microfluidic device includes a reagent inlet 562 in fluid communication with a reagent storage area 564, which may include, for example, one or more channels and/or reservoirs. The device may also include a sample inlet 565, sample loading area 566, and reaction area 568. The reaction area, which may include one or more areas for detecting a component in a sample, may be in fluid communication with waste area 570, and may be coupled to outlet 572. In some embodiments, reaction area 568 is an immunoassay area.

Figure 7A:
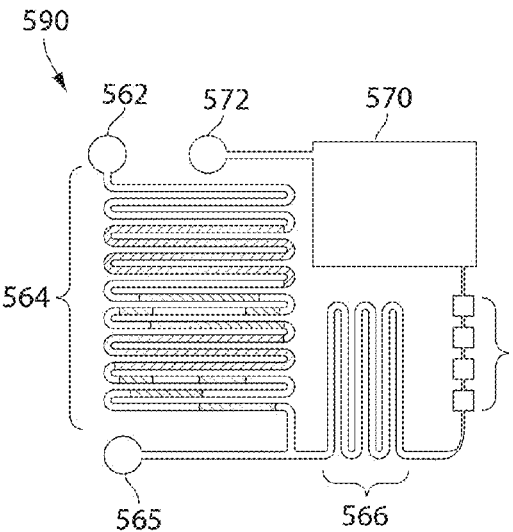
FIGS. 7A-7D are schematic diagrams of a microfluidic device that can be used with an open-ended fluidic device to perform a chemical and/or biological reaction according to an embodiment of the invention.
Figure 7B:
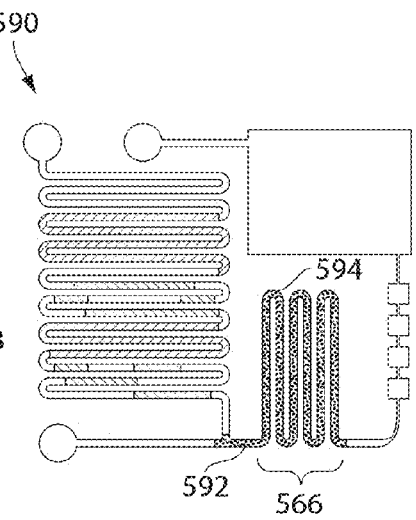
Figure 7C:
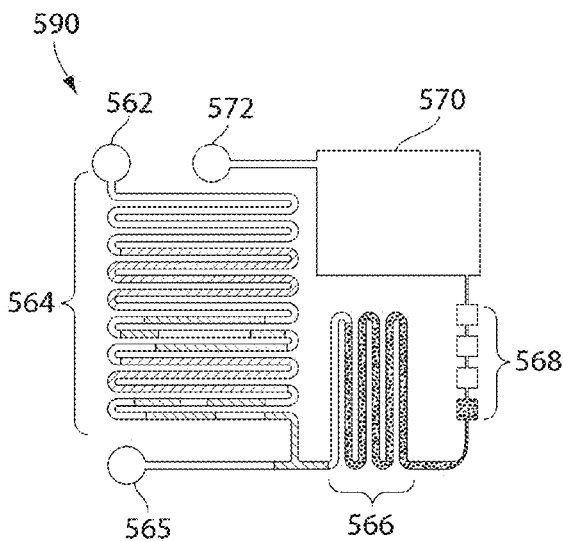
Figure 7D:
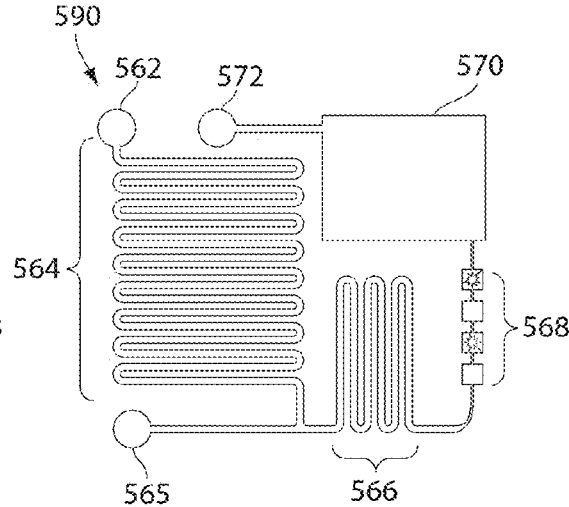

FIGS. 7A-7D show an example of a microfluidic system having the features described in FIG. 6. Microfluidic system 590 is compatible with an open-ended fluidic device for introducing a sample into the system. In FIG. 7A, fluid reagents are stored in reagent storage area 564 and dry reagents are stored in reaction area 568. Inlets 562 and 565, and outlet 572 are sealed prior to use. As shown in the embodiment illustrated in FIG. 7B, a seal over sample inlet 565 can be pierced, removed, or broken to allow a sample 592 to be introduced into sample inlet 565, which can flow into sample loading area 566, which may include an empty meandering channel 594. Flow of the sample may take place initially by capillary forces. Optionally, a seal may be placed over sample inlet 565 and a vacuum can be applied to outlet 572 to cause fluid flow towards the outlet (FIG. 7C). The sample flows into reaction area 568, followed by the stored fluid reagents from reagent storage area 564. As shown in FIG. 7D, after all of the reagents have passed through the reaction area, they may be contained in waste area 570 (or, optionally, may exit out of the device via the outlet).

As described herein, fluids (e.g., samples) can be introduced into a microfluidic device using a variety of devices such as an open-ended fluidic device and/or a fluidic connector. Although several configurations of such devices are shown in FIGS. 8-13, it should be understood that the invention is not limited to these configurations and that other configurations and/or arrangements are possible. Additionally, although descriptions herein involving sample introduction components (e.g., open-ended fluidic devices and fluidic connectors) primarily describe introduction of samples to microfluidic substrates, such components can be used to introduce any suitable substance such as reagents (e.g., buffers, amplification reagents, a component of a two-part system), gases, and particles.

For devices used in point-of-care settings, the sample introduction components may be designed to protect the user from occupational hazards. Additionally, the complexity of the sample-handling step may be minimized to allow the use of the device outside medical laboratories. These factors may be considered when choosing a particular design for a sample introduction component.

Sample introduction components such as open-ended fluidic devices and fluidic connectors may include any suitable article having a fluid path disposed therein. The sample introduction component (as well as other channels of the microfluidic system) may have a consistent or variable inner diameter and may have a length-to-internal diameter ratio of, for example, greater than 10 to 1, greater than 50 to 1, or greater than 100 to 1. Depending upon the application, sample introduction components (or microfluidic channels) of any diameter may be used, and in many applications it may have an inner diameter of, for example, less than 1 cm, less than 5 mm, less than 1 mm, less than 500 microns, less than 200 microns, less than 100 microns, or less than 50 microns. A sample introduction component (or microfluidic channel) with a greater length-to-internal diameter ratio may be useful in visually indicating the amount of each fluid contained in the component (or microfluidic channel). For instance, a linear measurement of a fluid plug in a fluidic device or fluidic connector of known inner diameter may give an accurate indication of the volume or the relative volume of the fluid. In some embodiments, the sample introduction component comprises a tube. Tubes are readily available in different diameters, lengths and materials. Tubes may be flexible and may be translucent or transparent. Fluid plugs in a tube may be measured linearly as an indication of the volume of the plug.

The sample introduction component, if a tube or another shape, may include two or more branches or sections that may be in fluid communication with each other and with the remaining interior of the component. In some embodiments, a tube may have two, three, four or more branches that may be interconnected. The branches and branch junctions may or may not include valves. Valves may be used to temporarily segregate one or more branches, and any liquid contained therein, from the remainder of the tube.

In some embodiments, a sample introduction component such as an open-ended fluidic device or a fluidic connector includes a volume control element. The volume control element can allow a fluid to fill a portion, but not all, of a fluid path of a sample introduction component. The volume control element can be used to meter a particular volume of fluid for introduction into a microfluidic system. In one embodiment, a volume control element is a frit, which can be placed inside a fluid path of a sample introduction component to stop further fluid from being introduced inside the fluid path after the fluid reaches a particular volume. The volume of fluid (e.g., sample) in the sample introduction component can be defined by the volume of the fluid path between the entry point (e.g., an inlet) for fluid introduction and the frit; the remaining volume may be occupied by air.

In another embodiment, a volume control element includes one or more metering marks that indicate up to which point(s) a fluid should be introduced into the fluid path. The volume of fluid in the fluid path may be controlled by the user.

In yet another embodiment, a volume control element includes a change in diameter (e.g., widening) of a fluid path within the sample introduction component. For instance, an open-ended fluidic device or a fluidic connector may include a first end (e.g., an opening), a first portion of a fluid path having a first diameter, a second portion of the fluid path having a second diameter, followed by a second end (e.g., an opening). The second diameter may be greater than the first diameter. The first diameter may be favorable for causing fluid to flow into the fluid path via capillary forces, while the second diameter may be less favorable (or unsuitable) for capillary action. Accordingly, a fluid may enter the first portion of the fluid path via the first end and the fluid may stop entering the fluid path when it reaches the second portion of the fluid path. In this embodiment, the volume of fluid (e.g., sample) in the sample introduction component can be defined by the volume of the first portion of the fluid path; the remaining volume (e.g., the second portion of the fluid path) may be occupied by air. Those of ordinary skill in the art know how to determine diameters of fluid paths that are favorable or less favorable for capillary action.

In yet another embodiment, a volume control element includes a patterned surface within a fluid path of the sample introduction component. For instance, a sample introduction component may include a first end (e.g., an opening), a first portion of a fluid path having a first, hydrophilic surface, a second portion of the fluid path having a second, hydrophobic surface, followed by a second end (e.g., an opening). The first, hydrophilic surface can cause a hydrophilic fluid (e.g., an aqueous fluid) to flow into the fluid path via capillary forces, while the second, hydrophobic surface is less favorable for capillary action. Accordingly, a fluid may enter the first portion of the fluid path via the first end and the fluid may stop entering the fluid path when it reaches the second portion of the fluid path. In this embodiment, the volume of fluid (e.g., sample) in the sample introduction component can be defined by the volume of the first portion of the fluid path; the remaining volume (e.g., the second portion of the fluid path) may be occupied by air. In one particular embodiment, a hydrophilic portion of the fluid path is defined by the presence of an anti-coagulant (e.g., heparin, a chelator (e.g., ethylenediamine tetraacetic acid, EDTA) or citrate), and a hydrophobic portion of the fluid path is defined by the absence of an anti-coagulant (or the presence of one or more hydrophobic molecules). Methods and materials for patterning surfaces of fluid paths are known by those of ordinary skill in the art.

In some embodiments, a sample introduction component such as an open-ended fluidic device or fluidic connector can include a combination of volume control elements such as the ones described above. A sample introduction component including one or more volume control elements can be filled using any suitable method such as by capillary forces, application of a vacuum, application of a positive pressure, and by use of valves.

As described in more detail below, sample introduction components can be connected to a substrate using a variety of methods. For example, a sample introduction component and/or substrate may include one or more of the following: pressure-fittings, friction-fittings, threaded connectors such as screw fittings, snap fittings, adhesive fittings, clips, magnetic connectors, or other suitable coupling mechanisms.

FIG. 8A shows an example of an open-ended capillary tube 700 (e.g., open-ended fluidic device) that can be used for introducing a sample into an inlet of a device (e.g., sample inlet 565 of FIG. 7A). Tube 700 may have an open end 704 (e.g., for inserting into an inlet of a device); end 702 may either be opened or closed. As shown in FIG. 8B, a capillary tube 710 can also be used as a fluidic connector to connect two channels (or portions of a channel) of a microfluidic system, e.g., as described in connection with FIG. 3. Tube 710 can include opened ends 712 and 714. The use of a capillary bent to form a "U"-shape is one of many possible devices that can be used to connect two channels (or portions of a channel).

The devices of FIGS. 8A and 8B can be made of any suitable material (e.g., a polymer or ceramic) and may be rigid or flexible. Non-limiting examples of such materials include glass, quartz, silicon, PTFE (Teflon), polyethylene, polycarbonate, poly(dimethylsiloxane), PMMA, polystyrene, a cyclo-olefin copolymer (COC) and cyclo-olefin polymer (COP). In certain embodiments where the tubes are formed of a flexible material, the tube may be placed in a holder of a sufficiently rigid material to maintain the tube in its final shape. For example, as shown in the embodiment illustrated in FIG. 8C, tube 720 may be positioned in groove 732 of holder 730 to maintain the shape of the tube. Optionally, a cover 734 may be used to cover the holder and may be attached to the holder, for example, by sealing, gluing, bonding, using adhesives, or by mechanical attachment (e.g., clipping into the holder). In other embodiments, instead of positioning the tube in a groove, the holder may include raised features (e.g., clips) for securing the tube. Ends 722 and 724 may be exposed to allow connection to one or more channels of a microfluidic system (FIG. 8D).

In another embodiment, an open-ended fluidic device (e.g., a capillary tube) or a portion of a fluidic connector can be made of a radiation-sensitive material such as a flexible plastic that hardens upon exposure to heat or UV light. After folding or bending the device in the desired shape (e.g., a "U"-shape), exposure to the appropriate radiations can cause the capillary to maintain its new shape.

In yet another embodiment, instead of bending straight capillaries to form a U-shape design, the open-ended fluidic device or fluidic connector can be manufactured directly in its final form. One example includes a capillary made of glass blown in the curved shape, which can allow sample loading onto the microfluidic device and/or fluid connection between channels or portions of a channel. Other manufacturing techniques and materials, including injection molding or extrusion of plastics, can also be used.

As shown in the embodiments illustrated in FIGS. 9A-9F, monolithic devices 800 and 830 having hollow, elongated volumes (e.g., microchannels 804) may be used as fluidic connectors. The devices may be rigid (e.g., for avoiding the need for the user to bend a capillary) and may optionally include a handle for simple handling (e.g., a vertical handle 810 as shown in FIG. 9B or a lateral handle 812 as shown in FIG. 9E). In such embodiments, a loop of tubing of an U-shaped capillary can be replaced by microchannels 804 having any suitable dimensions formed in a substrate 816. The dimensions of the microchannels can be tuned to accommodate a wide range of volumes of fluid (e.g., 1-1000 µL). Such devices can be filled entirely with a fluid (e.g., sample) or may be filled partially with fluid (e.g., using a volume control element to meter the amount of fluid in the fluid path). Moreover, the dimensions of the microchannels can also be chosen to allow the introduction of the fluid in the channels with capillary forces, or alternatively, the fluid can be aspirated using vacuum.

The channels may be covered by a cover (e.g., covers 820 and 822), which may be, for example, a block, an adhesive film, or a tape. The device presented in FIGS. 9A-9C may require a bonding step (e.g., by use of an adhesive) between cover 820 and substrate 816. In some embodiments, such a bonding step may avoided by applying a cover 822 such as an adhesive film (e.g., tape) over the surface of the device (FIGS. 9D-9F).

As illustrated in FIGS. 9A and 9D, devices 800 and 830 may include access ports 806 and 808 (e.g., inlets and outlets) that can allow a fluid to be introduced into the fluid path and/or to enable fluid communication between channels (or portions of a channel) of a microfluidic system. The access ports can have any suitable shape to allow formation of a tight seal with the ports of the microfluidic system. As shown in the embodiments illustrated in FIG. 9, the ports may have a conical shape that are complementary to conical apertures of a microfluidic device.

In some embodiments, once a fluidic connector is connected to a microfluidic device (e.g., the devices shown in FIGS. 1, 3, and 4), a vacuum is applied to an outlet of the device to cause fluid flow in the system. In these embodiments, the vacuum may strengthen the quality of the seal between the complementary ports.

Another example of a fluidic connector is shown in FIGS. 10A and 10B. In the embodiments illustrated in FIGS. 10A and 10B, fluidic connector 852 is prepared by assembling two parts 850. Fluidic connector 852 shows the implementation of a fluid path 855 within a rigid substrate 858, although in other embodiments, any arbitrary geometry can be used including a meandering channel configuration. The inlet and outlet ports 862 and 864 may be part of a conical protrusion 865 to form an air-tight seal with the conical apertures of the microfluidic chip. As described in more detail below, a more elaborate connection system can be implemented, such as snapping mechanisms or non-conical fittings. The fluidic connector can be optimized to allow simple handling for the user (including the addition of a handle to the design), if desired.

In some embodiments described herein, the fluidic connector is connected to a microfluidic device (e.g., a substrate including microfluidic channels disposed therein), by inserting the ports of the fluidic connector in access holes located directly above the microchannel(s) of the substrate. As a result, the fluid path of the fluidic connector may be in a plane orthogonal to the plane of the microchannels of the substrate, as shown in FIG. 11A. In some applications, however, there are advantages to placing the fluidic connector in the same plane as the microchannel network (e.g., using a lateral connection). One advantage of this configuration may be to maximize the area available for observation of the microfluidic device (e.g., for highly parallel assays). Another advantage may be to allow stacking of a large number devices on top of each other while allowing each device to be accessible to fluid dispensers or other instruments, which can save storage space in an instrument. In such embodiments, a fluidic connector 872 may be connected to an end portion 876 of a substrate 880. In other cases, the fluidic connector may be connected to a substrate at an angle between 90 and 180 degrees or between 0 and 90 degrees. Accordingly, fluidic connectors described herein may be connected to a substrate in any suitable configuration.

The reliability and simplicity of forming a good (e.g., fluid-tight) seal between a fluidic connector and a microfluidic substrate is a critical design aspect of a device for its use in point-of-care settings. In that regard, the fluidic connector or the substrate itself can include additional features to help the user insert the device onto or into the microfluidic substrate. For instance, in one embodiment, the fluidic connector includes at least one non-fluidic feature complementary to a feature of the substrate so as to form a non-fluidic connection between the fluidic connector and the substrate upon attachment. The non-fluidic complementary feature may be, for example, a protruding feature of the fluidic connector and corresponding complementary cavities of the microfluidic substrate, which can help the user align the fluidic connector with the substrate. Moreover, these guiding features can also help maintain the device in place. In other instances, the substrate includes protruding features complementary to cavities of the fluidic connector. In yet another embodiment, a device includes an alignment element associated with the substrate and constructed and arranged to engage with the fluidic connector and thereby position the connector in a predetermined, set configuration relative to the substrate. Examples of these and other features are described in more detail below.

FIGS. 12A-12E illustrate embodiments that enable attachment of a fluidic connector to a microfluidic substrate by snapping the two components together to form a connection. This configuration may be especially useful for applications involving point-of-care diagnostics, since the snapping mechanism may enable a good seal between the components, and may decrease the chance of the user mishandling the diagnostic test. The noise and/or feel experienced by the user while snapping the fluidic connector into the substrate can be used as a guide or control for successful attachment of the components.

Figure 12A:
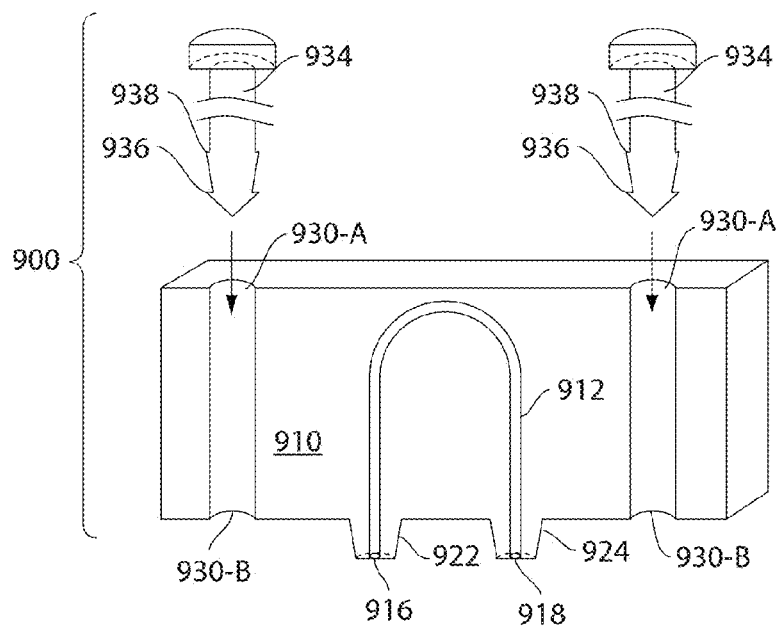
FIGS. 12A-12E are schematic diagrams of a fluidic connector including clips that can be used to attach the fluidic connector to a substrate according to an embodiment of the invention.
Figure 12B:
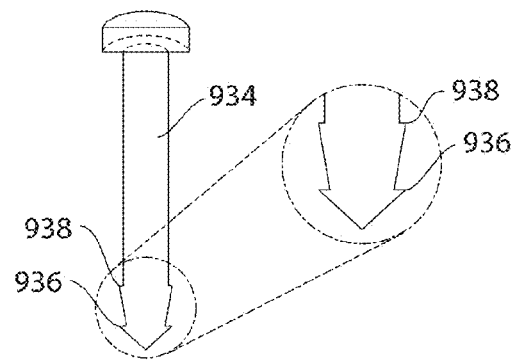

As illustrated in FIG. 12A, a fluidic connector 900 can include two identical first portions 910 (only one is shown) that form a fluid path 912 upon closing both halves against each other. In other instances, the fluidic connector includes a single integral piece including a fluid path 912 disposed therein. End portions 916 and 918 (e.g., an inlet and outlet) of the fluid path may be connected to a microfluidic substrate (not shown) via features 922 and 924, which may be complementary to features of the substrate. The fluidic connector may also include openings 930 for inserting clips 934. The clips may include two or more snap features (e.g., indentations) 936 and 938; these features may be formed of any suitable material (e.g., a polymer) and may be formed of the same or a different material than that of the clip and/or the substrate. Feature 938 may be used to connect the clip to first portion 910, and feature 936 may be used to connect the clip to the microfluidic substrate. Such features may allow the clip to be irreversibly attached to the fluid connector and/or to the substrate. FIG. 12B illustrates a magnified view of the clip. In other embodiments, the fluidic connector can be manufactured with the snap features, which can be directly a part of 910; for example, the fluidic connector may include feature 936 without the use of clip 934 (not shown).

Figure 12C:
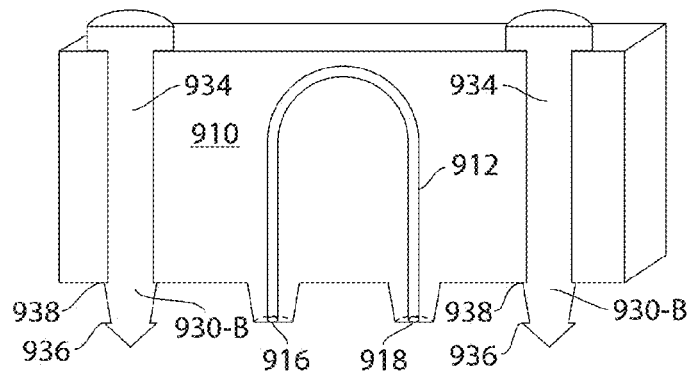
Figure 12D:
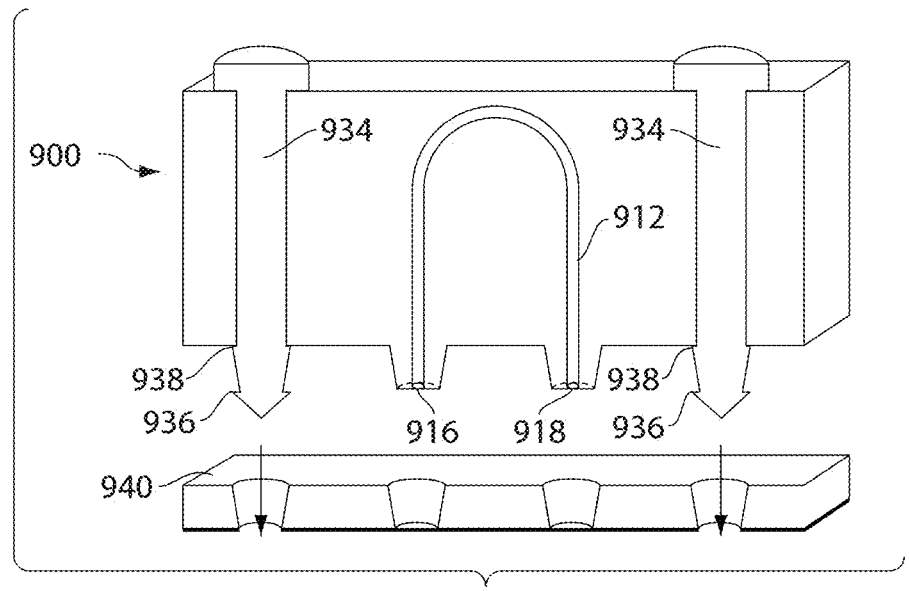
Figure 12E:
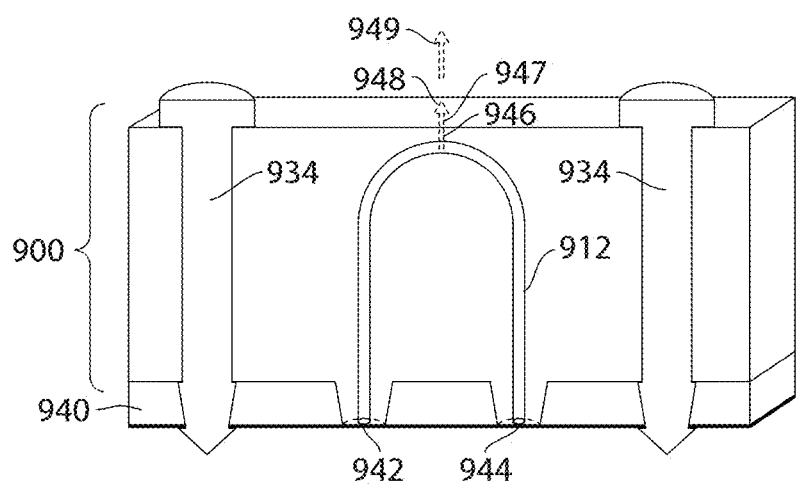

As shown in the embodiment illustrated in FIG. 12C, once a clip is inserted into openings 930 (e.g., when feature 938 meets opening 930-B), the clip may be attached to portion 910 of the fluidic connector. Likewise, as illustrated in FIG. 12D, the fluidic connector may be inserted into a portion of a microfluidic substrate 940 to cause attachment of the fluidic connector to the substrate (FIG. 9E). The snap features can guide the fluidic connector to the correct position in the microfluidic substrate. As described in more detail below, the attachment of a fluidic connector to a substrate may be reversible or irreversible. This attachment can cause fluid communication between a first channel at position 942 of the substrate and a second channel (or a portion of the first channel) at position 944 of the substrate via fluid path 912. As described herein, the fluidic connector may be loaded with a sample (e.g., via end portion 916 or 918) before or after attachment.

Figure 13:
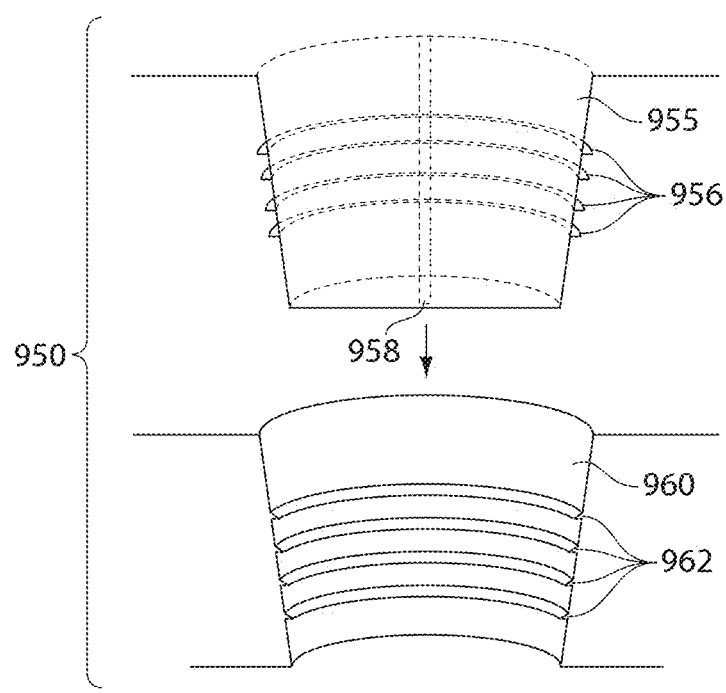
FIG. 13 is a schematic diagram of features that can be included on, for example, a fluidic connector and/or a substrate to secure attachment between the connector and substrate according to an embodiment of the invention.

As an alternative to the snapping mechanism described in connection with FIGS. 12A-12E, a fluidic connector can be attached to a microfluidic substrate using a zip-tie mechanism, as illustrated in FIG. 13. FIG. 13 shows a component 955 including features 956 (e.g., protrusions) that are complementary to portion 960, which includes features 962 (e.g., indentations). Component 955 may be a part of a fluidic connector and portion 960 may be part of a microfluidic substrate. In some instances, component 955 includes a fluid path 958 disposed therein.

Although features for connecting an article and a substrate, such as those shown in FIGS. 9, 10, 12 and 13, are described in reference to fluidic connectors and substrates, such features may also be used for connecting other articles of a device. For instance, such features may be used for connecting components such as an open-ended fluidic device and a substrate, a substrate and a cover, and/or multiple substrate layers of a device.

In embodiments described herein involving an article (e.g., a fluidic connector) comprising at least one feature complementary to a feature of the substrate, the features may be designed to form a reversible connection between the article and the substrate. Such embodiments may be useful, for example, for reusable devices. In other embodiments, such complementary features form an irreversible connection between the article and the substrate. The irreversible connection may cause the article and the substrate to be integrally connected. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, or separating components fastened together via adhesives or tools. Devices including features forming an irreversible connection may be useful, for example, for one-time-use (e.g., disposable) devices. Such devices may form an irreversible connection so that the user cannot interfere with a chemical and/or biological reaction being performed in the device after connection.

The examples illustrated in FIGS. 12 and 13 include more than two connections (e.g., fluidic or non-fluidic connections) between a fluidic connector and a microfluidic substrate. This characteristic may be useful because additional points of connection (e.g., non-fluidic connections) can increase the stability of the attachment against mechanical stress (e.g., due to handling by the user) and shocks (e.g., improper use of the device). Additionally, each additional point of connection can increase the area of contact between the fluidic connector and the substrate, while the area associated with forming the fluid-tight seal between the fluidic connector and the substrate can remain unchanged. Alternatively, a single non-fluidic connection may be sufficient to yield good sealing properties.

Although many embodiments described herein include sample introduction components (e.g., fluidic connectors) having a single fluid path, it should be understood that a sample introduction component may include more than one fluid path and/or branching fluid paths. For example, as shown in the embodiment illustrated in FIG. 12E, fluidic connector 900 may optionally include a secondary flow path 946, which connects inlet 947 to flow path 912. This design can allow, for example, the introduction of a fluid into fluid flow path 912 via inlet 947 and secondary path 946 after fluidic connector 900 has been connected to a substrate. Alternatively, a fluid can be introduced into fluid path 912 via inlet 947 prior to connection of the fluidic connector and substrate.

In addition, sample introduction components such as fluid connectors described herein may include one or more sampling elements used to receive a fluid sample from a biological entity. The sampling element may be in the form of a needle or swab, for example. The sampling element may be reversibly or irreversibly attached to a sample introduction component. In some instances, the sampling element can puncture a biological component. For instance, as shown in the embodiment illustrated in FIG. 12E, fluidic connector 900 may include a (sterilized) sampling element 948, e.g., in the form of a hollow, sharp point (e.g., a needle), that may be used to puncture a component such as human skin. This configuration can allow the sampling element to receive a fluid sample from the biological component and can enable transfer of a fluid from the biological entity to fluid path 912 (e.g., by capillary forces). After fluid has been introduced into inlet 947, secondary fluid path 946 can be blocked, e.g., using component 949, which may have a shape complementary to that of fluid path 946. This blocking can prevent fluid from re-entering the secondary fluid path such that there is only one fluid path for flow. This arrangement can also prevent the user from being exposed further to sampling element 948.

In another embodiment, component 949 (optionally including a fluid path) can be used to obtain a sample, and upon insertion of the component into secondary fluid path 946, the sample can be transferred from the component to fluid path 912. In certain embodiments, insertion of the component prevents fluid from re-entering the secondary fluid path such that there is only one fluid path for flow.

In some embodiments, a sample introduction component includes a sampling element connected directly to a primary fluid path. For instance, in the embodiment illustrated in FIG. 10, conical protrusions 865, which may be complementary to a feature of a microfluidic substrate, may include sampling elements at the ends that can allow puncture of a biological component. Sampling elements may also be present as part of an open-ended fluidic device (e.g., as shown in FIG. 8A) and/or other fluidic connectors described herein (e.g., FIG. 8B).

Devices described herein may optionally include an alignment element associated with the substrate. The alignment element may be constructed and arranged to engage with the fluidic connector and thereby position the fluidic connector in a predetermined, set configuration relative to the substrate. As shown in the embodiments illustrated in FIGS. 14A and 14B, device 964 may include a substrate 966, a fluidic connector 968, and an alignment element 980. Substrate 966 may include a microfluidic system such as one described herein, e.g., as shown in FIGS. 1-7, 11, 17-18. The microfluidic system may comprise, for example, at least a first microfluidic channel including an inlet and an outlet and a second microfluidic channel including an inlet and an outlet (not shown). Fluidic connector 968, which may have a configuration as described herein and may be constructed for matching connection to the substrate. The fluidic connector may include a fluid path 970 having a fluid path inlet 972 and a fluid path outlet 974. Upon connection of the fluidic connector to the substrate, the fluid path inlet may connect to the outlet of the first microfluidic channel of the substrate, and the fluid path outlet 974 may connect to the inlet of the second microfluidic channel of the substrate. This connection can result in fluid communication between the first and second microfluidic channels of the substrate.

Figure 14A:
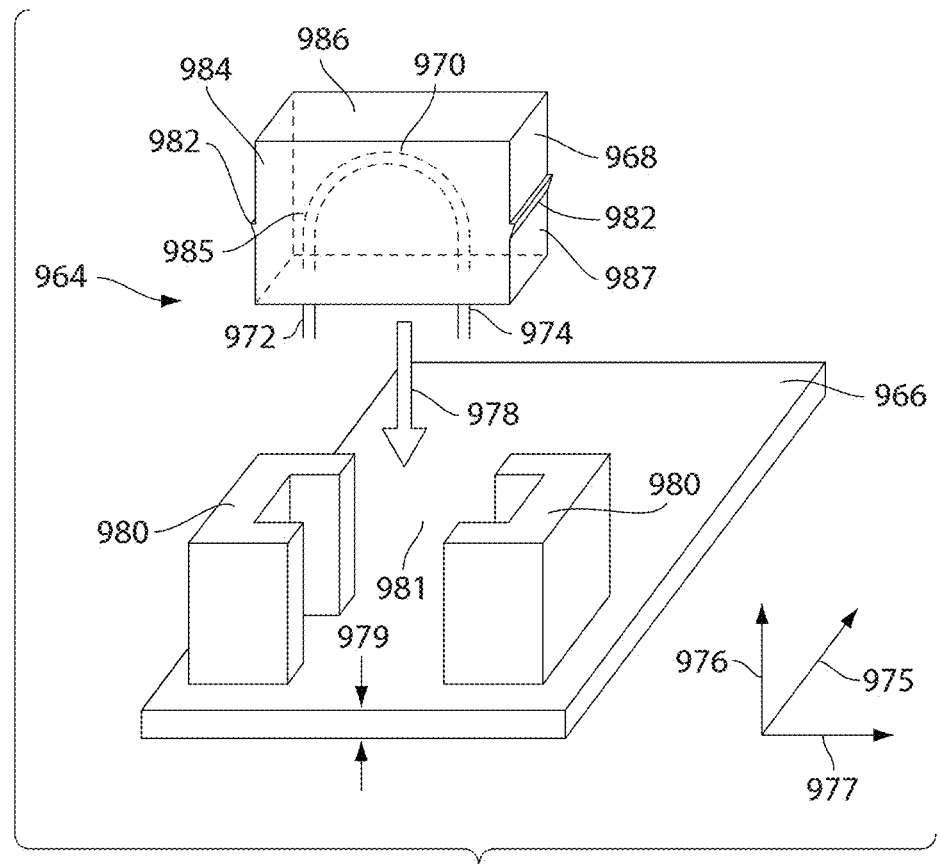
FIGS. 14A and 14B are schematic diagrams showing a perspective view of a device including an alignment element, a fluidic connector, and a substrate according to an embodiment of the invention.
Figure 14B:
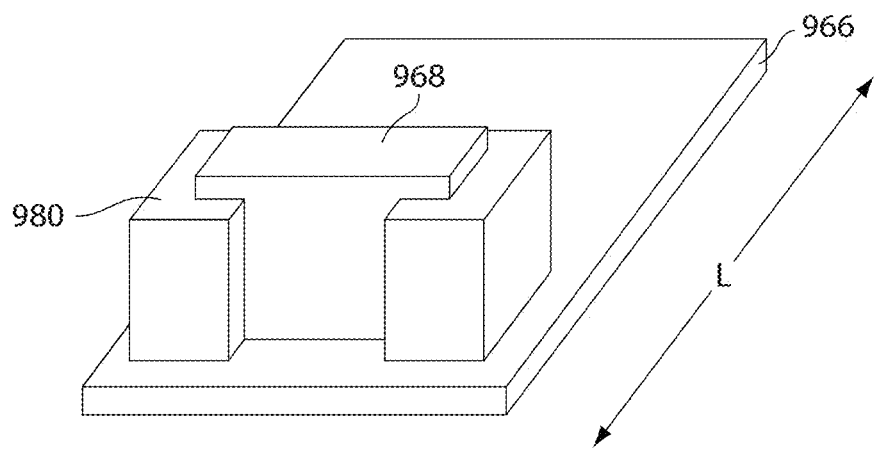

As shown in the illustrative embodiments of FIGS. 14A and 14B, the device may include an alignment element 980 associated with the substrate and extending approximately perpendicular to the substrate. For example, while substrate 966 (as well as the first and second microfluidic channels) lies generally in the plane defined between arrows 975 and 977, alignment element 980 extends generally perpendicular to the substrate in the plane defined by arrows 975 and 976. In other embodiments, the alignment element may extend approximately parallel to the substrate.

As illustrated, alignment element 980 includes a cavity 981 constructed and arranged to receive and engage the fluidic connector and thereby position the connector in a predetermined, set configuration relative to the substrate. The cavity may have a depth of, for example, at least 0.5 cm, at least 1 cm, at least 1.5 cm, at least 2 cm, or at least 3 cm (e.g., as measured from the position of the fluid path inlet and/or fluid path outlet upon engagement of the fluidic connector and the alignment element.). The cavity may have a depth similar or equal to the height of the fluidic connector. The cavity does not necessarily have to encompass all sides of the fluidic connector, as long as it is constructed and arranged to receive and engage the fluidic connector and thereby position the connector in a predetermined, set configuration relative to the substrate.

In some embodiments, the configuration of the alignment element and the fluidic connector may be adapted to allow insertion of the fluidic connector into the alignment element by a sliding motion. For example, the fluidic connector may slide against one or more surfaces of the alignment element when the fluidic connector is inserted into the alignment element.

An alignment element may have any suitable configuration for engaging a fluid connector. In some embodiments, the alignment element (or a cavity of an alignment element) may be in contact with 1, 2, 3, 4 or more surfaces, e.g., surfaces 984, 985, 986, and/or 987, of the fluid connector upon engagement. One or more surfaces of the alignment element in contact with the fluidic connector may extend from the substrate, e.g., along the planes defined between arrows 976 and 977, between arrows 976 and 975, and therebetween.

In addition, all or portion of the alignment element may have a height, thickness, or a depth (e.g., for insertion of a fluidic connector) that may be, for example, greater than or equal to at least 1, 2, 3, 4, 5, etc., times the thickness 979 of the substrate. The alignment element may have a height or thickness of, for example, at least 0.5 cm, at least 1 cm, at least 1.5 cm, at least 2 cm, or at least 3 cm (e.g., as measured from the position of the fluid path inlet and/or fluid path outlet upon engagement of the fluidic connector and the alignment element). A larger height/thickness of the alignment element may allow, in some embodiments, further stabilization and/or guidance of the fluidic connector into the alignment element. The dimensions can vary and may depend on a variety of factors such as the dimensions of the fluidic connector and the substrate.

Optionally, the alignment element may include one or more engaging components that may engage a portion of the fluidic connector. FIG. 14A shows the fluidic connector having engaging components 982. The engaging component may have a height of, for example, at least 0.5 cm, at least 1 cm, at least 1.5 cm, or at least 2 cm as measured from the position of the fluid path inlet and/or fluid path outlet upon engagement of the fluidic connector and the alignment element.

In some cases, the alignment element includes an engaging component complimentary to an engaging component of the fluidic connector. An engaging component may include, for example, a groove or other indentation, a protrusion (e.g., as shown in FIG. 13), and/or a mechanism such as o-ring that may be at least partially deformable. It should be understood that an engaging component may have any suitable shape and/or form. In some cases, an engaging component creates a substantial resistance to movement of the fluidic connector relative to the substrate and/or alignment element upon the alignment element receiving the fluidic component (e.g., upon insertion of the fluidic component into the alignment element) and/or during intended use of the device. For example, the single act of inserting fluidic connector 968 into the cavity of alignment element 980 may cause the engaging components of the fluidic connector and alignment element to interact, thereby creating a substantial resistance to movement of the fluidic connector relative to the substrate and/or alignment element. Therefore, in certain embodiments, separate clamps or other fastening mechanisms, and/or secondary steps for fastening, are not required.

In some embodiments, the engaging component causes the fluidic connector to be integrally connected to the alignment element. In one particular embodiment, engaging components are snap features that may clip into a feature of the alignment element (or fluidic connector). Such and other features can allow, in some embodiments, the fluidic connector to be irreversibly attached (e.g., integrally connected) to the alignment element and/or to the substrate. In other cases, the alignment element and the fluidic connector are designed to be reversibly attached to one another. Accordingly, an engagement component may facilitate the engagement of the fluidic connector and the substrate in a predetermined, set configuration relative to the substrate upon their connection.

In some embodiments, the configuration of a cavity and/or an engaging surface of an alignment element causes the fluid path of the fluid connector to lie approximately perpendicular to the substrate (and, therefore, approximately perpendicular to the microfluidic channels within the substrate). For example, as illustrated in FIGS. 14A and 14B, fluid path 970 is approximately perpendicular to the substrate in the plane defined by arrows 975 and 976. In other embodiments, a fluid path of the fluid connector lies at an angle between 90 and 180 degrees or between 0 and 90 degrees relative to the substrate.

Although FIGS. 14A and 14B show alignment element 980 positioned at one end of the substrate, in other embodiments, an alignment component can extend along the length, L, of the substrate, e.g., towards opposing ends of the substrate. For example, the alignment component may be a block having a length and width similar to that of the substrate, but may include a cavity where the fluidic connector is to be inserted. Furthermore, although FIGS. 14A and 14B show alignment element 980 in the form of two components, in some embodiments an alignment element may be in the form of a single component. In other embodiments, the alignment element is in the form of more than two components.

Figure 15A:
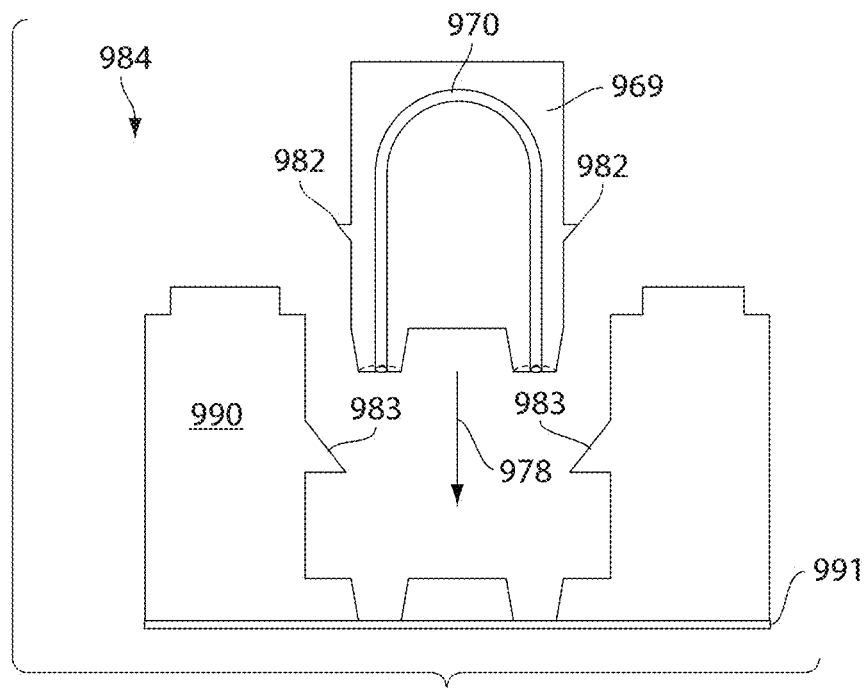
FIGS. 15A and 15B are schematic diagrams showing a cross-sectional view of a device including an alignment element that and a substrate that are formed of a single part according to an embodiment of the invention.
Figure 15B:
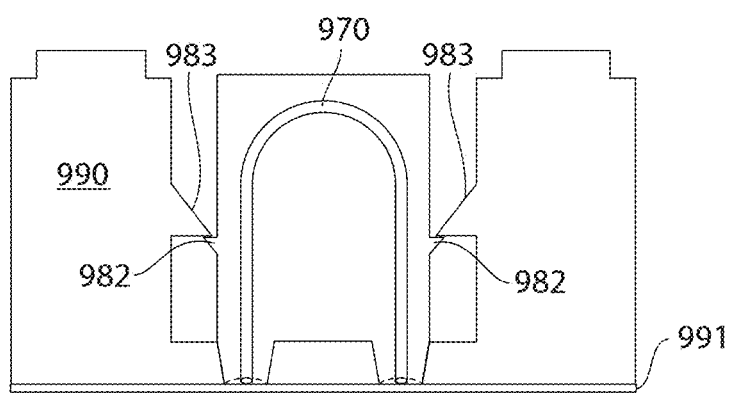

In some embodiments, the alignment element and the substrate are in the form of a single piece of material, which, in some cases, can be fabricated in one step, e.g., by injection molding. For example, as shown in the exemplary embodiment of FIGS. 15A and 15B, alignment element 990 may be part of a substrate 991 containing a microfluidic system.

Figure 16A:
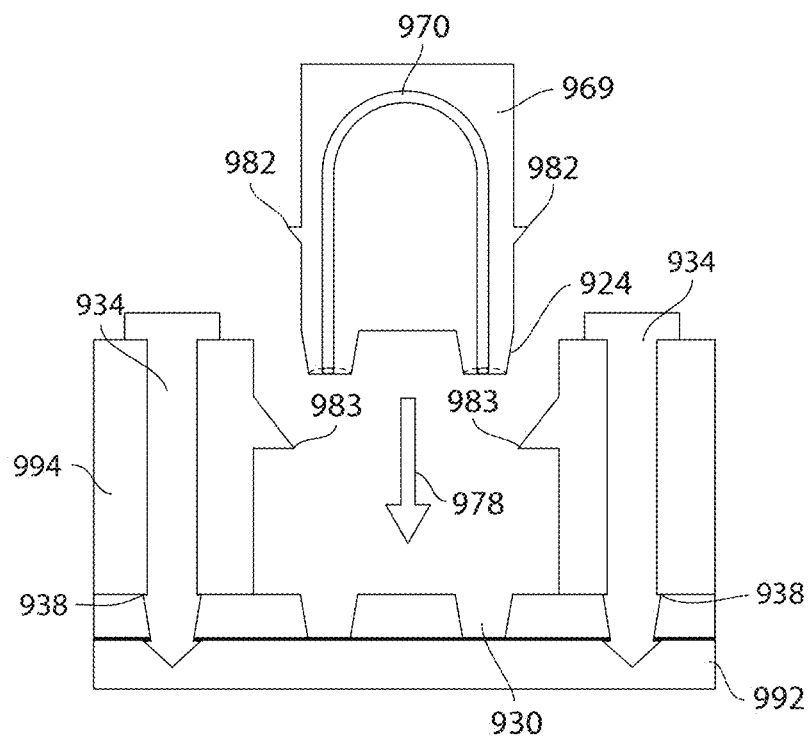
FIGS. 16A and 16B are schematic diagrams showing a cross-sectional view of a device including an alignment element that and a substrate that are formed of separate parts according to an embodiment of the invention.
Figure 16B:
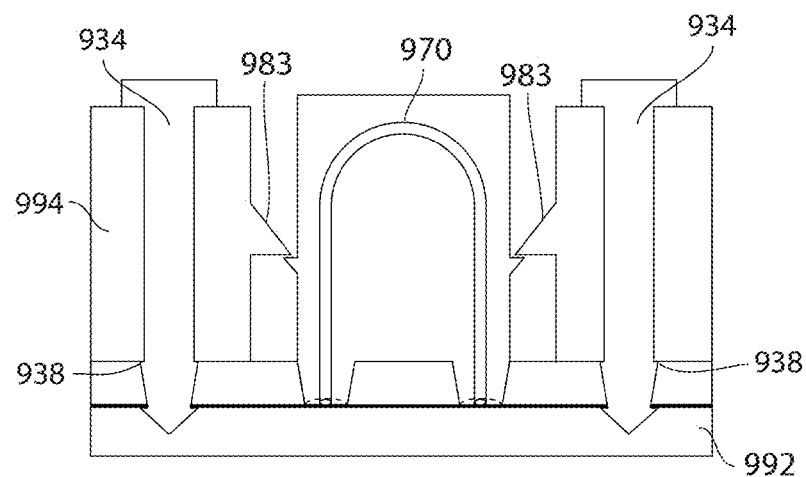

In contrast, as shown in the exemplary embodiment of FIGS. 16A and 16B, a substrate 992, which includes a microfluidic system, and an alignment element 994 are separate parts that can be joined together prior to use. The alignment element and the substrate may be connected by inserting clips 934 into portions of the substrate, e.g., as described in connection with FIGS. 12A and 12B. This connection may be performed prior the user receiver using the device. In other instances, the user can insert the alignment element into the substrate, followed by the fluidic connector into the alignment element. Alternatively, the user may insert the fluidic connector into the alignment element, followed by the alignment element into the substrate.

FIGS. 14 and 15 also show an alignment element including engaging components 983, which engage with engaging components 982 of the fluidic connector. The device may be configured such that a fluidic connector 969 can be inserted into the alignment element in the direction of arrow 978, while preventing or inhibiting removal of the fluidic component from the alignment element after insertion (e.g., in the opposite direction of arrow 978).

It should be understood that alignment elements may be combined with other features described herein. For example, an alignment element may be associated with a fluidic connector that includes at least one non-fluidic feature complementary to a feature of the substrate so as to form a non-fluidic connection between the fluidic connector and the substrate upon attachment, e.g., as described in connection with FIGS. 1 and 12.

There are several advantages of using microfluidic devices with fluidic connectors, especially when performing chemical and/or biological reactions (e.g., immunoassays) in the device. Accordingly, devices described herein may have one or more advantages such as: (a) use of small amounts of sample with little or no sample waste, (b) long-term stability of chemical and/or biological reagents stored in the device, (c) reduction of cross-contamination between stored reagents and/or between sample and reagent, (d) sample metering, (e) ease of use to untrained users for introducing a sample into the device, (f) efficient mixing of reagents, and (g) assay reliability. In some embodiments, the devices have all of the advantages listed above.

Small amounts of sample can be used with little or no sample waste because fluidic connectors (as well as open-ended fluidic devices) can be designed to have an internal volume matching the volume of sample required for performing the chemical and/or biological reaction. This can reduce the amount of dead volume in a system. Optionally, as described above, fluidic connectors and open-ended fluidic devices can include one or more volume control elements to allow collection of a particular volume of sample.

Devices described herein may be used for point-of-care applications, and can be manufactured several months (or years) prior to first use. In some embodiments requiring storage of components in the device prior to first use, it is important that all biomolecules and reagents introduced at the time of manufacturing remain stable for extended periods of time. For example, in a reaction area, capture antibodies can be physisorbed to the surface of the microchannels, and can be stabilized in a dry form using stabilizers (e.g., trehalose).

It has been demonstrated previously that the storage of the reagents in the form of liquid plugs separated by air gaps were stable for extended periods of time (see, for example, International Patent Publication No. WO2005/072858 (International Patent Application Serial No. PCT/US2005/003514), filed Jan. 26, 2005 and entitled "Fluid Delivery System and Method," which his incorporated herein by reference in its entirety).

Both liquid and dry reagents may be stored on a single microfluidic substrate. As described herein, in some embodiments, a channel containing a liquid reagent is not in fluid communication with a channel containing a dry reagent since, depending on the particular environmental (e.g., storage) conditions, if the channels containing the reagents are in fluid communication with one another, transport of water vapors can result in the wet reagent drying out and dry molecules being hydrated. This can affect the long-term stability of all reagents stored on certain devices. A system involving the use of a fluidic connector and a microfluidic substrate including dry reagents physically separated (e.g., in different channels) and not in fluidic communication with the wet reagents can allow fluid communication only at the time of use of the microfluidic device. This configuration can enhance the stability of the reagents for long-term storage. In other embodiments, however, liquid and dry reagents can be stored in fluid communication with one another (e.g., for shorter-term storage).

Another advantage of microfluidic devices described herein may be reduction of cross-contamination between stored reagents and/or between sample and reagent. Cross contamination may occur, in certain embodiments, at intersections between microfluidic channels, where plugs of reagents can get caught. These reagents can contaminate subsequent reagents flowing past the same intersection. The use of a fluidic connector can greatly simplify a microchannel network, reducing or obviating the number of intersection(s) on a device, and thus any potential cross-contamination problems.

Sample metering is another important requirement for many microfluidic applications. Often this is performed off-chip and an accurate sample volume is loaded onto the chip with the hope that the entire volume will flow inside the device. With fluidic connectors described herein, the volume of sample that can be introduced inside the microfluidic device can be accurately measured, and the entire volume of sample can be sent to a reaction area of the device.

As described herein, several designs of sample introduction components (e.g., fluidic connectors and open-ended fluidic devices) can be used by untrained users (see, for example, the embodiments described in connection with FIGS. 8-16). These components can be designed to facilitate the sample loading procedure and to allow simple attachment of a fluidic connector to a microfluidic substrate. Such devices may be especially useful in point-of-care settings by untrained users.

Another advantage of systems and methods described herein may include efficient mixing of reagents on a device. An example of efficient mixing has been described herein in connection with silver enhancement chemistry based on the reduction of silver ions by a reducing agent (e.g., hydroquinone) by a catalyst (e.g., a noble metal). In embodiments involving immunoassays, secondary antibodies can be labeled with gold colloids (catalyst). In the presence of a mixture of silver ions and hydroquinone, multiple layers of silver can be created at the surface of the gold colloid, increasing the size of the colloid. After about 10 minutes of amplification, the size of the colloid can increase by a factor of, for example, about 1000, yielding on the surface grains of silver that can be observed with an optical setup. To achieve good amplification results (e.g., a large signal amplification with little amplification of background), the amplification reagent can be stored separately, e.g., in separated channels or containers, and mixed only immediately before use. In microfluidic devices, the cross-sectional dimensions of the channel may be small and flows may be laminar, meaning mixing occurs primarily by diffusion, which is typically inefficient and slow. However, the laminar character of the flow of reagents may be decreased when traveling through a fluid path of a fluid connector, since the fluid path may have a relatively larger cross-sectional dimension (and, therefore, a relatively larger volume) than the that of the microchannels of the substrate. Accordingly, in certain embodiments, each fluid connector can act as a chaotic mixer and can significantly improve the mixing of two or more reagents. In the example described above, this mixing can improve the reproducibility of the amplification chemistry.

In some embodiments described herein, microfluidic devices include only a single interconnected channel with, for example, less than 5, 4, 3, 2, or 1 channel intersection(s) when in use (e.g., upon attachment of a fluidic connector and a substrate). A layout based on a single channel with minimal or no intersections may be reliable because there is only one possible flow path for any fluid to travel across the microfluidic chip. In these configurations, the reliability of a chemical and/or biological reaction to be performed in the device is greatly improved compared to designs having many intersections. This improvement occurs because at each intersection (e.g., a 3-way intersection or more), the fluid has the potential to enter the wrong channel. The ability to load a sample without channel intersections can eliminate risk of fluid entering the wrong channel. Because an intersection may represent a risk factor that must be taken into account in product development, controls (either on-chip or based on external inspection) must be set up to insure correct fluid behavior at each interconnection. In certain embodiments described herein, the need for such additional controls can be alleviated.

As described above, reagents can be stored in a microfluidic device using a variety of methods. Such methods may depend at least in part on the form in which the reagent is stored (e.g., dried or wet), the configuration of the channels within microfluidic system (e.g., whether the channels are interconnected or unconnected), the length of time of storage, and/or the particular application.

Referring back to FIG. 2, in some embodiments, a first reagent (or series of reagents) is positioned in a first channel formed in a substrate, such as in a channel or reservoir of reagent storage area 64. A second reagent (or series of reagents) may be positioned in a second channel formed in a substrate, such as a channel or reservoir of immunoassay area 68. In some cases, the first and second channels are not in fluid communication with one another during the positioning of the reagents. The first and/or second reagent may be positioned in their respective channels by first flowing the reagents in the channels and then sealing any inlet(s) and/or outlet(s) of the channels.

The first and/or second reagents may be substantially altered after being positioned in their respective channels. For instance, in some cases the first and/or second reagents is dried after flowing the reagent(s) in a channel. Optionally, the dried reagents may be treated with a third reagent (e.g., a blocking agent) which may, for example, reduce non-specific adsorption during carrying out of an assay. The dried reagent(s) may be stored in a channel by sealing one or more inlets and/or outlets of the microfluidic channel.

In some instances, a reagent is positioned in a channel prior to complete fabrication of a microfluidic channel system. A microfluidic channel system is not complete if, for example, a system that is designed to have enclosed channels has channels that are not yet completely enclosed. A channel is enclosed if at least one portion of the channel has a cross-section that is completely enclosed, or if the entire channel is completely enclosed along its entire length with the exception of its inlet(s) and/or outlet(s).

In some embodiments, one or more reagents is positioned on a detection zone of a substrate by placing a droplet of the reagent at the detection zone (e.g., detection zones 162, 164, 166, and 168 of FIG. 3). The substrate may be formed of a hydrophobic material, which can prevent spreading of aqueous reagents across adjacent detection zones. The reagents at the detection zones may be dried and a cover may be placed adjacent the substrate to complete fabrication of the channel system. Subsequently, any inlet(s) and/or outlet(s) of the channel can be sealed.

In another embodiment, one or more reagents is positioned (e.g., patterned) on a cover, and then the cover is used to enclose a microfluidic channel system formed in a substrate. The reagents on the cover may be aligned with certain areas within the microfluidic system. For instance, in one particular embodiment, reagents (e.g., antibodies) are patterned in an arrangement (e.g., shape and dimension) that is matched with detection zones 162, 164, 166, and 168 of FIG. 3. The reagents can be dried, and then the cover can be sealed against the substrate such that the reagents are positioned in the detection zones of the microfluidic system. The cover can be, for example, a biocompatible adhesive (e.g., prepared on a substrate) and can be made of a polymer (e.g., PE, COC, PVC) or an inorganic material. For some applications, the material and dimensions of a cover are chosen such that the cover is substantially impermeable to water vapor. In other embodiments, the cover can be non-adhesive, but may bond thermally to the microfluidic substrate by direct application of heat, laser energy, or ultrasonic energy. Any inlet(s) and/or outlet(s) of the channel can be sealed (e.g., by placing an adhesive over the inlet(s) and/or outlet(s)) after introducing reagents into the device.

Wet reagents are typically stored in a microfluidic system after channels of the system have been completely covered. A fluid reagent to be stored in the system may be introduced into an inlet of a channel, and after at least partially filling the channel with the fluid, the inlet(s) and/or outlet(s) of the channel can be sealed, for example, to retain the fluid and to prevent contamination from external sources.

In some instances, one or more fluids to be stored in a microfluidic system is transferred from a vessel (e.g., a cartridge, tube, or fluidic connector) to the microfluidic system. The vessel may contain, for example, two or more distinct fluids separated by a third fluid that is immiscible with both. Any number of distinct fluids may be contained in a vessel. For example, in one embodiment, the vessel is a tube that includes a reagent solution plug followed by an air plug, followed by a rinse solution plug. An additional air plug may separate the first rinse solution plug from a second rinse solution plug. The liquid plugs may retain their relative positions in the tube and may be prevented from contacting each other by the interspaced air plugs. Articles and methods for delivering fluids to a microfluidic system are described in more detail in International Patent Publication No. WO2005/072858 (International Patent Application Serial No. PCT/US2005/003514), filed Jan. 26, 2005 and entitled "Fluid Delivery System and Method," which his incorporated herein by reference in its entirety.

Using a vessel containing fluid plugs in linear order can allow introduction of fluid from the vessel to a microfluidic system in a particular sequence. These fluids can then be stored in the particular sequence in the microfluidic system (e.g., in a reagent storage area). The inlet(s) and/or outlet(s) of the channel containing the fluids can be sealed, for example, to retain the fluid and to prevent contamination from external sources. In some embodiments, a particular sequence of fluids is contained in a fluidic connector. For example, the particular sequence of fluids may include reagents (e.g., a sample, a buffer, a component that binds with the sample, etc.) positioned in series and may be optionally separated by immiscible fluids. This sequence of fluids can be introduced into a microfluidic substrate by fluidly connecting the fluidic connector and the substrate.

In some embodiments, a microfluidic channel or fluidic connector having a relatively large length-to-internal diameter ratio (or high surface area to volume ratio) is used to store one or more fluids. This configuration can allow a linear measurement of one or more fluid plugs in a fluidic device or fluidic connector of known inner diameter, and may give an accurate indication of the volume or the relative volume of the fluid. This feature may be useful for determining if an accurate or correct amount of fluid is contained in a channel, especially after long-term or short-term storage of one or more fluids in the channel. For example, if the channel has a relatively large length-to-internal diameter ratio (e.g., greater than 10 to 1, greater than 50 to 1, or greater than 100 to 1), a user may be able to determine if an accurate or correct amount of fluid is contained in the channel by simple inspection, since the loss of fluid (e.g., by evaporation) can result in air bubbles or the presence of empty portions in the channel. If such air bubbles or empty portions are present, or the amount of fluid in the channel it outside of a range indicated on the device, the user may be warned (e.g., by instructions that accompany the device) that the device should not be used. This visual inspection may be difficult in certain devices that use reservoirs having relatively a small length-to-internal diameter ratio (or a low surface area to volume ratio) for storing fluids.

Reagents can be stored in a microfluidic system for various amounts of time. For example, a reagent may be stored for longer than 1 hour, longer than 6 hours, longer than 12 hours, longer than 1 day, longer than 1 week, longer than 1 month, longer than 3 months, longer than 6 months, longer than 1 year, or longer than 2 years. Optionally, the microfluidic system may be treated in a suitable manner in order to prolong storage. For instance, microfluidic systems having stored reagents contained therein may be vacuum sealed, stored in a dark environment, and/or stored at low temperatures (e.g., below 0 degrees C.). The length of storage depends on one or more factors such as the particular reagents used, the form of the stored reagents (e.g., wet or dry), the dimensions and materials used to form the substrate and cover layer(s), the method of adhering the substrate and cover layer(s), and how the device is treated or stored as a whole.

As described herein, different sections of a microfluidic channel or reservoir, especially within a reaction area, can be each modified with a different species (e.g., capture molecule) that can be stored in the channel or reservoir, so that a sample traveling throughout the microchannel channel can travel successively over each of the species. The sections of the microfluidic channel may be, for example, detection zones (e.g., meandering channel regions) as described herein in connection with FIGS. 2-7 and 14-17. In some embodiments, these sections are connected in series. In other embodiments, the sections are connected in parallel. In yet other embodiments, a device may include a combination of sections connected in series and parallel. In embodiments including detection zones connected in series (and/or in parallel), multiple components of the sample can be tested individually in each of the detection zones of the channel. The detection zones may have different configurations depending on the application; for example, a detection zone may be in the form of a reservoir (which may be supported by an array of pillars) or a meandering channel region, as described in further detail below. In certain embodiments, a device includes a plurality (e.g., at least 2, 4, 6, 8, 10, or more) of sections, each section comprising a single chemical and/or biological species that can undergo a chemical and/or biological reaction (or which may be unreactive towards particular components of a sample, as in a negative control). The chemical and/or biological species in one section may be the same (e.g., same species and concentration) or different (e.g., different species and/or concentration) as the species of another section.

To simplify signal quantification, each detection zone (e.g., meandering channel region) may have a relatively large area compared to a cross-sectional dimension of a microfluidic channel of the system. For example, the detection zone may have an area of greater than 0.1 mm$^2$, greater than 0.2 mm$^2$, greater than 0.4 mm$^2$, greater than 0.6 mm$^2$, greater than 0.8 mm$^2$, or greater than 1 cm$^2$. The area may be, for example, between 0.1 mm$^2$ to 0.3 mm$^2$, between 0.2 mm$^2$ to 0.4 mm$^2$, between 0.4 mm$^2$ to 0.6 mm$^2$, or between 0.5 mm$^2$ to 1 cm$^2$. Different proportions of the detection zone may comprise an optical detection pathway. For example, at least 20%, at least 40%, at least 50%, at least 60%, or at least 80% of the area of the detection zone may comprise an optical detection pathway. The area spanned by the detection zone may be defined by the rectangular area bound by outermost points of the detection zone along each axis. A signal produced in the detection zone may be homogeneously spread over a large area, thus simplifying the alignment of an optical readout device.

Figure 17A:
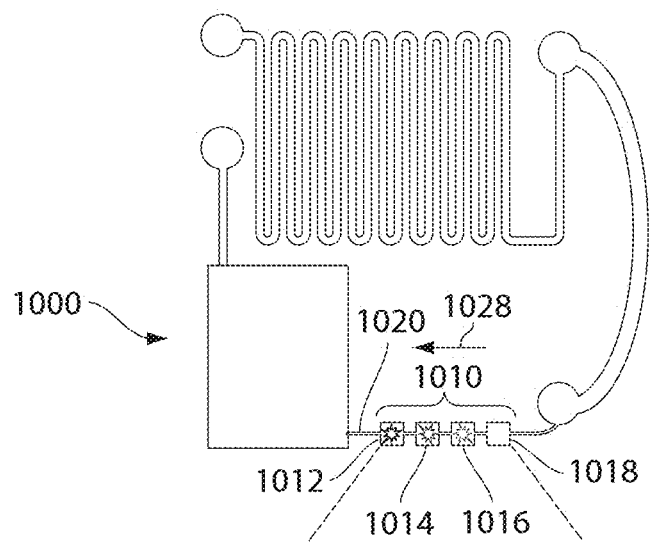
FIGS. 17A-17C are schematic diagrams of a device including detection zones in the form of meandering regions according to an embodiment of the invention.
Figure 17B:
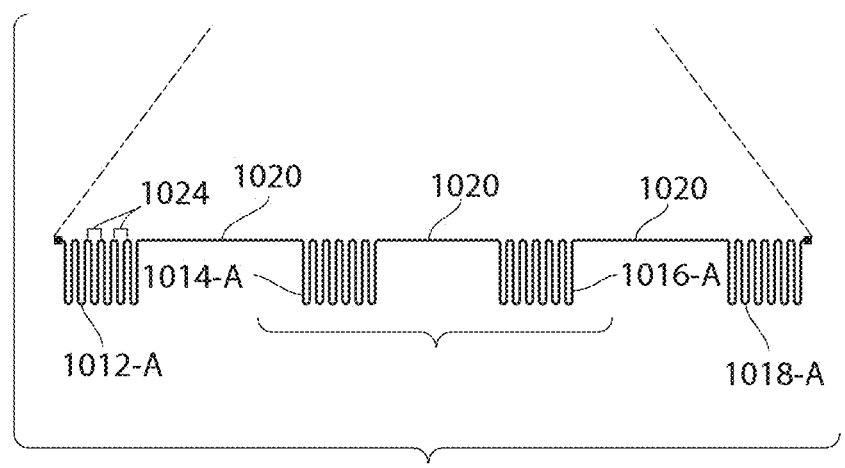
Figure 17C:
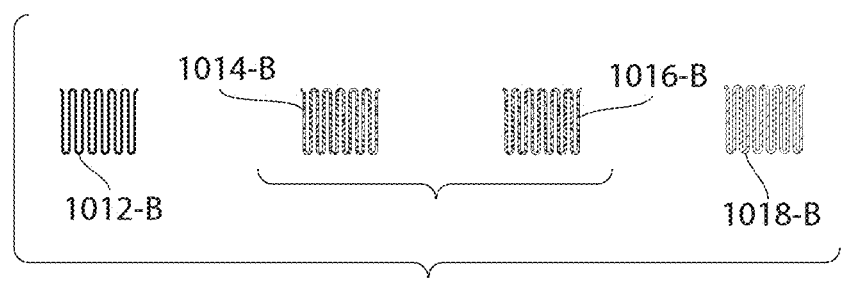

As shown in the embodiments illustrated in FIGS. 17A-17C, device 1000 may include a reaction area 1010 having several detection zones 1012, 1014, 1016, and 1018. Each of these detection zones may be in the form of a meandering region 1012-A, 1014-A, 1016-A, and 1018-A, respectively (FIG. 14B). The meandering regions include several channel segments 1024. The meandering regions can be connected to one another (i.e., in fluid communication with one another) via microfluidic channel 1020. Fluid flowing in channel 1020, e.g., in the direction of arrow 1028, can flow through the meandering regions sequentially.

As described herein, a surface of the meandering channel in each meandering region can be modified with one or more biomolecules (e.g., in the form of a stored reagent) for a particular application. To provide on-chip quality control, meandering region 1018-A can be modified with a blocking solution such as BSA or Tween 20 to provide a negative reference for the assay. In a similar fashion, meandering region 1012-A can be modified with a positive control. The choice of these standards may be such that after successful assay completion, the negative standard should indicate no signal (or very weak background signal), and the positive signal should indicate a clear signal. In general, the choice of the reagent/biomolecule to be immobilized in each meandering region can be governed by the particular test to be performed; for example, for the measurement of total human IgG in serum, anti-human antibodies can be physisorbed in meandering regions 1014-A and 1016-A.

FIG. 17C is a schematic diagram showing the meandering regions after performing a chemical and/or biological reaction in the meandering regions. Meandering region 1018-B used as a negative control has a weak signal and appears light grey. Meandering regions 1014-B and 1016-B that included physisorbed reagents that can be used for determining a component in the sample may include a detectable signal (e.g., a gray film). Meandering region 1018-B used as a positive control may include a strong signal (e.g., a black film).

FIGS. 17A-17C show an example of a multiplex assay that can be performed in a microfluidic device described herein. In other embodiments, additional meandering regions (e.g., greater than 5, 8, 10, 15, or 20 meandering regions, which may be connected in series and/or parallel), can be included on a device to allow detection of additional components in a sample.

After performing a chemical and/or biological reaction in a detection zone (e.g., meandering region), a signal may appear in the detection zone. The type and strength of the signal may depend on the choice of label and/or amplification chemistry used. For example, in one embodiment, silver enhancement chemistry can be used to produce a signal that can be detected by a simple detector, such as the one described in International Patent Publication No. WO2005/066613 (International Patent Application Serial No. PCT/US2004/043585), filed Dec. 20, 2004 and entitled "Assay Device and Method", which is incorporated herein by reference in its entirety.

Figure 18A:
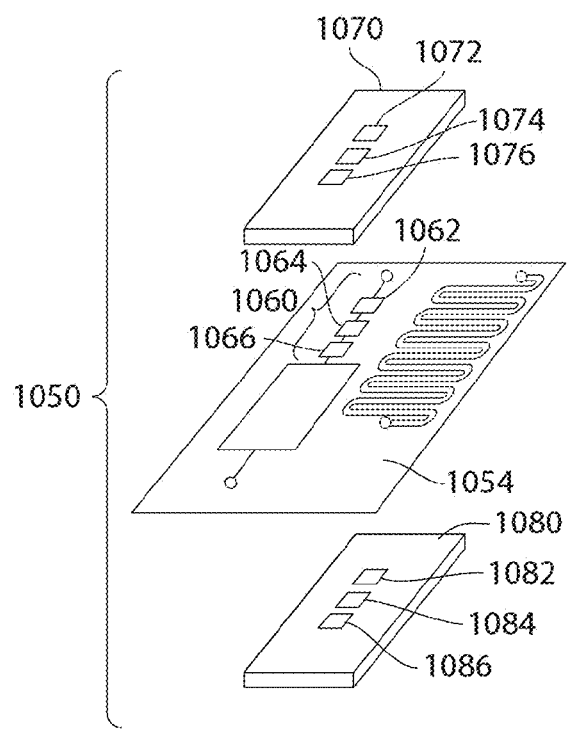
FIGS. 18A and 18B are schematic diagrams of an optical system for detecting a component in a detection zone of a device according to an embodiment of the invention.
Figure 18B:
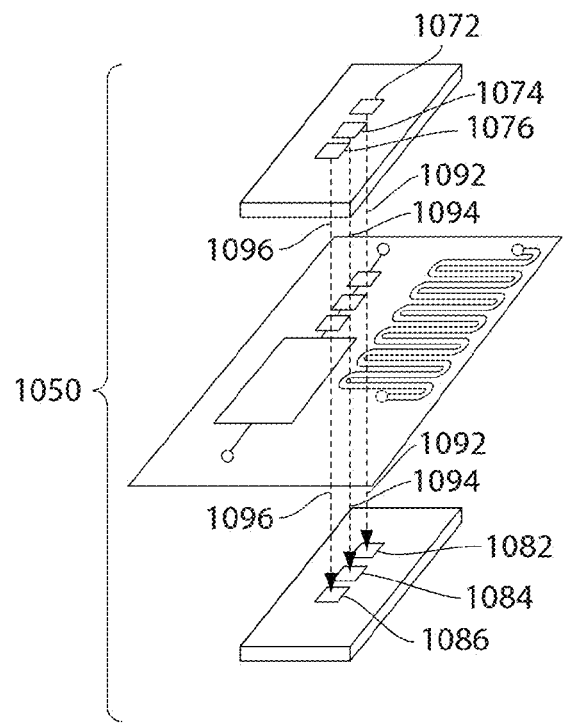

When more than one chemical and/or biological reaction (e.g., a multiplex assay) is performed on a device, the signal acquisition can be carried out by moving a detector over each detection zone. In an alternative approach, a single detector can detect signal(s) in each of the detection zones simultaneously. In another embodiment, an analyzer can include, for example, a number of parallel optical sensors/detectors, each aligned with a detection zone and connected to the electronics of a reader (e.g., FIGS. 18A and 18B). FIGS. 18A and 18B illustrate an optical system 1050 at rest (FIG. 18A) and during measurement (FIG. 18B). As shown in the embodiment illustrated in FIG. 18A, optical system 1050 includes a device 1054 having a detection area 1060 including detection zones 1062, 1064, and 1066. The optical setup also includes an article 1070 comprising an array of light sources 1072, 1074, and 1076, as well as an article 1080 comprising an array of detectors 1082, 1084, and 1086. In some embodiments, articles 1070 and 1080 are combined to form an analyzer. The light sources and detectors may be aligned with the detection zones of the device. During measurement, an optical pathway 1092 between optical light source 1072, detection zone 1062, and detector 1082 allows determination of a signal in the detection zone. Parallel optical pathways 1094 and 1096 can allow simultaneous determination of signals in detection zones 1064 and 1066, respectively.

Figure 19:
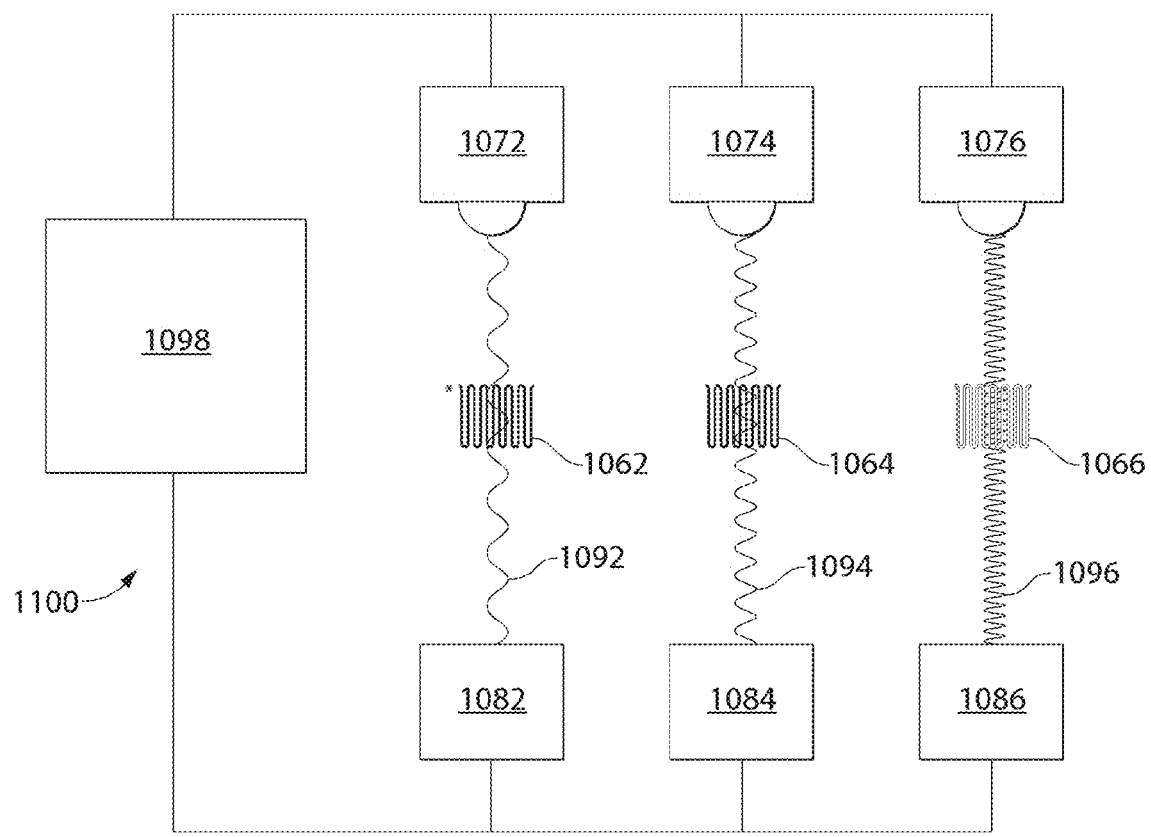
FIG. 19 is a schematic diagram of an optical system for detecting components in different detection zones of a device according to an embodiment of the invention.

The interior of an analyzer can be designed to allow simultaneous reading (e.g., detection or determination of a signal) in all detection zones without interference between each optical pathway in the system. For example, in the embodiment illustrated in FIG. 19, system 1100 includes light source 1072 and detector 1082 aligned with each other and detection zone 1062. Additionally, light source 1074 can be aligned with detection zone 1064 and detector 1084 and light source 1076 can be aligned with detection zone 1066 and detector 1086. The light sources and detectors may be in electronic communication with control unit 1098 (e.g., a microprocessor). In some embodiments, one or more optical filters can be positioned between a detector and a detection zone. Additionally and/or alternatively, each detector may include an electronic filter for filtering different wavelengths of light. To further reduce cross-talk between optical pathways, the light from each light source can be modulated at a frequency different for each optical pathway; that is, optical pathways 1092, 1094, and 1096 may each include light of different wavelengths. The electronic signal generated by light source 1072 can be differentiated from noise signal arising from by neighboring light sources 1074 and 1076 by using, for example, an electronic filter. In a different approach, the readout can be performed sequentially to avoid noise signal(s) arising from the neighboring light sources. Using a light source-detector pair for each detection zone may be advantageous when the optical components are relatively simple and/or inexpensive.

Figure 20:
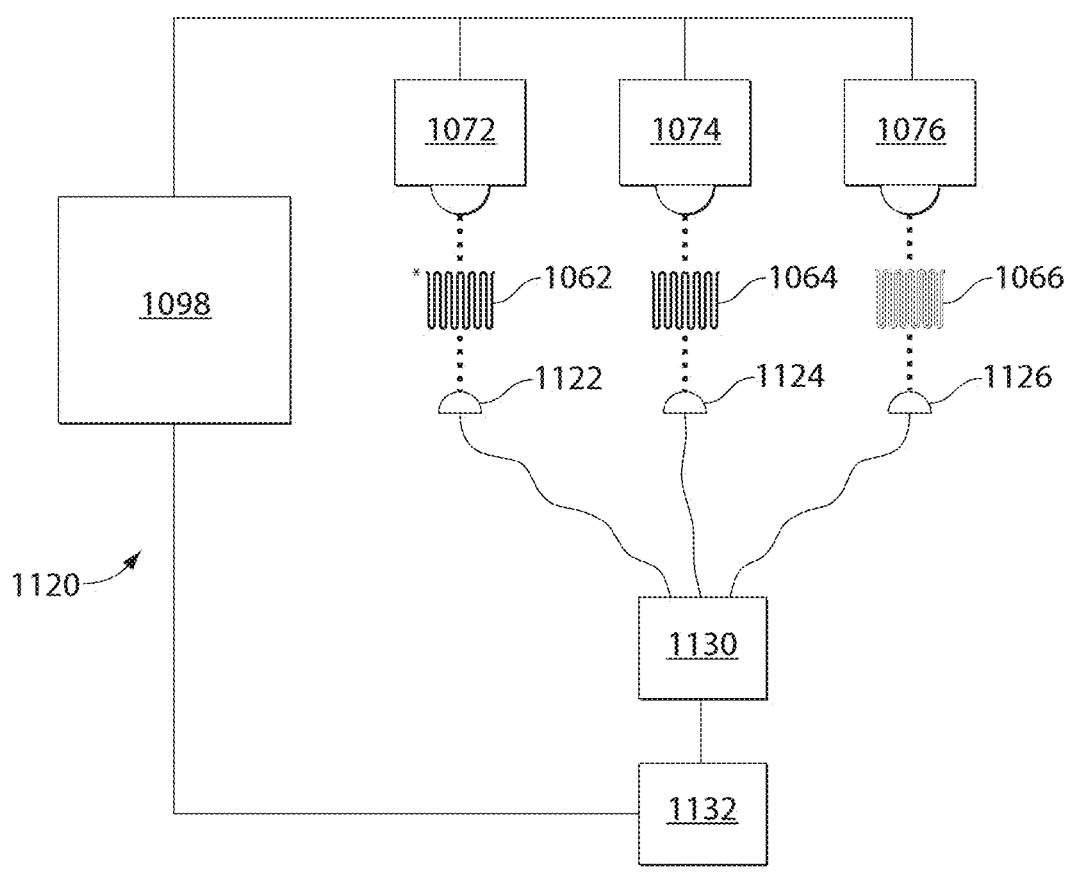
FIG. 20 is a schematic diagram of an optical system including an optical light source and a detector aligned with each detection zone of a device according to an embodiment of the invention.

In some embodiments, one or more optical components can be shared between detection zones. For instance, in the embodiment illustrated in FIG. 20, a system 1120 includes a detector 1072 and an optical element 1122 (e.g., a collecting optic such as an optical fiber), which are aligned with each other and with detection zone 1062. Similarly, the system includes a detector 1074 and an optical element 1124 aligned with detection zone 1064, as well as a detector 1076 and an optical element 1126 aligned with detection zone 1066. The optical elements may all be connected to an optical switch 1130 and to a common light detector 1132, such as an avalanche photodiode or a photomultiplier tube. The common detector may be used to detect signals in each of the detection zones (e.g., sequentially). The light from each detection zone can be collected by the optical elements, which can be aligned underneath each detection zone.

A variety of determination (e.g., measuring, quantifying, detecting, and qualifying) techniques may be used. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. Those of ordinary skill in the art know how to modify microfluidic devices in accordance with the determination technique used. For instance, for devices including chemiluminescent species used for determination, an opaque and/or dark background may be preferred. For determination using metal colloids, a transparent background may be preferred. Furthermore, any suitable detector may be used with devices described herein. For example, simplified optical detectors, as well as conventional spectrophotometers and optical readers (e.g., 96-well plate readers) can be used.

In some embodiments, determination techniques may measure conductivity. For example, microelectrodes placed at opposite ends of a portion of a microfluidic channel may be used to measure the deposition of a conductive material, for example an electrolessly deposited metal. As a greater number of individual particles of metal grow and contact each other, conductivity may increase and provide an indication of the amount of conductor material, e.g., metal, that has been deposited on the portion. Therefore, conductivity or resistance may be used as a quantitative measure of analyte concentration.

Another analytical technique may include measuring a changing concentration of a precursor from the time the precursor enters the microfluidic channel until the time the precursor exits the channel. For example, if a silver salt solution is used (e.g., nitrate, lactate, citrate or acetate), a silver-sensitive electrode may be capable of measuring a loss in silver concentration due to the deposition of silver in a channel as the precursor passes through the channel.

Different optical detection techniques provide a number of options for determining reaction (e.g., assay) results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. The system may be operated with a minimum of optical devices (e.g., a simplified optical detector). For instance, the determining device may be free of a photomultiplier, may be free of a wavelength selector such as a grating, prism or filter, may be free of a device to direct or columnate light such as a columnator, or may be free of magnifying optics (e.g., lenses). Elimination or reduction of these features can result in a less expensive, more robust device.

In one embodiment, the light source can be pulse modulated, for example, at a frequency of 1,000 Hz. To match the pulse modulated light source, a detector may include a filter operating at the same frequency. By using a pulse modulated light source it has been found that the system can be less sensitive to extrinsic sources of light. Therefore, an assay may run under various light conditions, including broad daylight, that might make it impractical to use existing techniques. Experimental results indicate that by using a pulse modulated light source and filter, results are consistent regardless of the light conditions under which the test is run.

The light source may be a LED (light-emitting diode) or a laser diode. For example, an InGaAlP red semiconductor laser diode emitting at 654 nm may be used. The photodetector may be any device capable of detecting the transmission of light that is emitted by the light source. One type of photodetector is an optical integrated circuit (IC) including a photodiode having a peak sensitivity at 700 nm, an amplifier and a voltage regulator. If the light source is pulse modulated, the photodetector may include a filter to remove the effect of light that is not at the selected frequency. When multiple and neighboring signals are detected at the same time, the light source used for each detection zone can be modulated at a frequency sufficiently different from that of its neighboring light source. In this configuration, the detector can be assorted with a filter of matching fervency (compared to its attributed light source), thereby avoiding interfering light form neighboring optical pairs.

As described herein, a meandering channel of a reaction area may be configured and arranged to align with a detector such that upon alignment, the detector can measure a single signal through more than one adjacent segment of the meandering channel. In some embodiments, the detector is able to detect a signal within at least a portion of the area of the meandering channel and through more than one segment of the meandering channel such that a first portion of the signal, measured from a first segment of the meandering channel, is similar to a second portion of the signal, measured from a second segment of the meandering channel. In such embodiments, because the signal is present as a part of more than one segment of the meandering channel, there is no need for precise alignment between a detector and a detection zone.

The positioning of the detector over the detection zone (e.g., a meandering region) without the need for precision is an advantage, since external (and possibly, expensive) equipment such as microscopes, lenses, and alignment stages are not required (although they may be used in certain embodiments). Instead, alignment can be performed by eye, or by low-cost methods that do not require an alignment step by the user. In one embodiment, a device comprising a meandering region can be placed in a simple holder (e.g., in a cavity having the same shape as the device), and the measurement area can be automatically located in a beam of light of the detector. Possible causes of misalignment caused by, for instance, chip-to-chip variations, the exact location of the chip in the holder, and normal usage of the device, are negligible compared to the dimensions of the measurement area. As a result, the meandering region can stay within the beam of light and detection is not interrupted due to these variations.

The detector may detect a signal within all, or a portion, of a detection zone (e.g., including a meandering region). In other words, different amounts of the meandering region may be used as an optical detection pathway. For instance, the detector may detect a signal within at least 15% of the detection zone, at least 20% of the detection zone, at least 25% of the detection zone, within at least 50% of the detection zone, or within at least 75% of the detection zone (but less than 100% of the detection zone). In some instances, 100% of the detection zone is used for detection by a detector (e.g., detection in a transparent channel by the unaided eye). The area in which the detection zone is used as an optical detection pathway may also depend on, for instance, the opacity of the material in which the channel is fabricated (e.g., whether all, or, a portion, of the channel is transparent), the amount of a non-transparent material that may cover a portion of the channel (e.g., via use of a protective cover), and/or the size of the detector and the detection zone.

In one embodiment, a signal produced by the reaction is homogenous over the entire detection zone (e.g., over an entire meandering channel region). That is, the detection zone (e.g., meandering channel region) may allow production and/or detection of a single, homogenous signal in said region upon carrying out a chemical and/or biological reaction (e.g., and upon detection by a detector). Prior to carrying out a reaction in the meandering channel region, the meandering channel may include, for example, a single species (and concentration of species) to be detected/determined. The species may be adsorbed to a surface of the meandering channel. In another embodiment, the signal may be homogeneous over only portions of the meandering region, and one or more detectors may detect different signals within each of the portions. In certain instances, more than one detection zone can be connected in series and each detection zone can be used to detect/determine a different species.

In some embodiments, a chemical and/or biological reaction involves binding. Different types of binding may take place in devices described herein. The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

In some cases, a heterogeneous reaction (or assay) may take place in a channel; for example, a binding partner may be associated with a surface of a channel, and the complementary binding partner may be present in the fluid phase. The term "binding partner" refers to a molecule that can undergo binding with a particular molecule. Biological binding partners are examples; for instance, Protein A is a binding partner of the biological molecule IgG, and vice versa. Likewise, an antibody is a binding partner to its antigen, and vice versa. In other cases, a homogeneous reaction may occur in the channel. For instance, both binding partners can be present in the fluid phase (e.g., in two-fluid laminar flow system). Non-limiting examples of typical reactions that can be performed in a meandering channel system include chemical reactions, enzymatic reactions, immuno-based reactions (e.g., antigen-antibody), and cell-based reactions.

In another embodiment of the invention, a microfluidic device developed to perform a specific clinical test is labeled with information specific to the test (e.g., name of the test, batch-specific data and expiration date). One or more components of the system, such as the sample introduction component, can be designed such that it is marked with patient-specific information (e.g., physically or electronically). Upon attachment of the sample introduction component to a microfluidic device (e.g., a microfluidic substrate, optionally in connection with other (e.g., electronic) components), the patient's information can become linked to the device and the particular test performed on the device. In some cases, e.g., for certain embodiments involving permanent attachment of the sample introduction component to a disposable microfluidic device (e.g., by zip tie or snapping mechanism as described above), the two sets of information (one from the sample introduction component and one from the microfluidic device) cannot be separated. This can provide a safe method for adding the patient's information onto the microfluidic device. For example, in one embodiment, a microfluidic device is labeled with test-specific information (e.g., name of the test, data for the test calibration, batch name and number), and the sample introduction component includes a surface that can accommodate a standard-sized sticker containing a code referring to the patient identity (e.g., a bar code).

Though in some embodiments, systems of the invention may be microfluidic, in certain embodiments, the invention is not limited to microfluidic systems and may relate to other types of fluidic systems. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" (e.g., a diameter) of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another set of embodiments, the maximum cross-sectional dimension of the channel(s) containing embodiments of the invention are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (e.g., a concave or convex meniscus).

A microfluidic substrate can be fabricated of any material suitable for forming a microchannel. Non-limiting examples of materials include polymers (e.g., polyethylene, polystyrene, polycarbonate, poly(dimethylsiloxane), and a cyclo-olefin copolymer (COC)), glass, quartz, and silicon. Those of ordinary skill in the art can readily select a suitable material based upon e.g., its rigidity, its inertness to (e.g., freedom from degradation by) a fluid to be passed through it, its robustness at a temperature at which a particular device is to be used, and/or its transparency/opacity to light (e.g., in the ultraviolet and visible regions). In some embodiments, the material and dimensions (e.g., thickness) of a substrate are chosen such that the substrate is substantially impermeable to water vapor.

In some instances, an microfluidic substrate is comprised of a combination of two or more materials, such as the ones listed above. For instance, the channels of the device may be formed in a first material (e.g., poly(dimethylsiloxane)), and a cover that is formed in a second material (e.g., polystyrene) may be used to seal the channels. In another embodiment, a channels of the device may be formed in polystyrene or other polymers (e.g., by injection molding) and a biocompatible tape may be used to seal the channels. A variety of methods can be used to seal a microfluidic channel or portions of a channel, including but not limited to, the use of adhesives, gluing, bonding, or by mechanical methods (e.g., clamping).

The following examples are intended to illustrate certain embodiments of the present invention, but are not to be construed as limiting and do not exemplify the full scope of the invention.

EXAMPLE 1

Fabrication of Microfluidic Channels in a Substrate

A method for fabricating a microfluidic channel system is described.

The layouts of the channel system were designed with a computer-aided design (CAD) program and are illustrated in FIGS. 3 and 4. The microfluidic devices were formed in poly(dimethylsiloxane) Sylgard 184 (PDMS, Dow Corning, Distrelec, Switzerland) by rapid prototyping using masters made in SU8 photoresist (MicroChem, Newton, Mass.). The masters were produced on a silicon wafer and were used to replicate the negative pattern in PDMS. The masters contained two levels of SU8, one level with a thickness (height) of ~50 µm defining the channels in the immunoassay area, and a second thickness (height) of ~250 µm defining the reagent storage and waste areas. The master was silanized with (tridecafluoro-1,1,2,2-tetrahydrooctyl)trichlorosilane (ABC-R, Germany). PDMS was mixed according to the manufacturer's instructions and poured onto the master. After polymerization (4 hours, 65°), the PDMS replica was peeled off the master and access ports were punched out of the PDMS using brass tubing with sharpened edges (1.5 mm in diameter). To complete the fluidic network, a flat substrate such as a glass slide, silicon wafer, polystyrene surface, flat slab of PDMS, or an adhesive tape was used as a cover and placed against the PDMS surface. The cover was held in place either by van der Waals forces, or fixed to the PDMS using an adhesive.

In other embodiments, the microfluidic channels were made in polystyrene by injection molding. This method is known to those of ordinary skill in the art.

EXAMPLE 2

Storing Reagents in a Microfluidic System

This example describes a method for storing dry and liquid reagents in a microfluidic system.

Dry and wet reagents were stored in the microfluidic systems shown in FIGS. 3-5 and 14. To store dry reagents, drops of biomolecules were placed onto the detection zones of the substrate. After 30 min, the solution was removed and the surface of the substrate modified with proteins was rinsed with buffer. The surface was dried with compressed nitrogen for 20 s, and then the substrate was sealed against a cover. The cover was either a plate of polystyrene (in the case PDMS substrates) (NUNC Omnitray, VWR, Switzerland) or a biocompatible adhesive (in the case of polystyrene substrates). When a biocompatible adhesive was used, the polystyrene substrate was drilled to obtain access holes prior to application of the cover. In a different approach, the holes were formed in the thermoplastic during the injection molding process by using pillars inside the cavity of the injection molding machine. All of the microchannels, including those of the reagent storage and immunoassay areas, were filled with blocking buffer (Tween 20 and/or BSA in phosphate buffered saline (PBS)) to render the surfaces of the microfluidic channels hydrophilic and to block the surfaces to avoid non-specific adsorption of protein on the walls of the microchannels. The blocking solution was removed by suction and the device was dried at room temperature under vacuum.

To store wet reagents in the microfluidic system, reagent solutions for an immunoassay were first prepared in separate containers (e.g., wells of a 96-well plate, or centrifuge tubes). The reagents were sequentially aspirated as liquid plugs, followed by air spacers between successive liquid plugs, into secondary tubing (polyethylene with a inner diameter of 0.2 mm) with a manually operated syringe connected to the back of the tubing.

Reagents were stored in channels of a reagent storage area of the microfluidic system (fabricated by the method described in Example 1) by connecting an outlet port of the tubing into an inlet of the channel. The fluids flowed from the tubing to the channel by either capillary forces, applying negative pressure (e.g., a vacuum) to the outlet of the channel, or by applying positive pressure to the inlet of the tubing (using a syringe plunger). The reagents resided in the reagent storage area of the channel.

The inlets and outlets of the channels were then sealed by placing a biocompatible adhesive over the inlets and outlets. In the case of a polystyrene substrate, this second tape was applied onto the surface opposite of the surface modified with the cover. This sealing protected the stored reagents from degradation/denaturation due to atmospheric conditions.

The reagents were stored in the microfluidic channels for three months without degradation/denaturation, as tested by use of the reagents in quantitative immunoassays. This example shows that both dry and liquid reagents (including proteins) can be stored for extended periods of time in microfluidic channels.

EXAMPLE 3

Performing an Immunoassay by Loading a Sample Using an Open-Ended Capillary Tube This example shows that an immunoassay can be performed by loading a sample using an open-ended capillary tube and using reagents stored on a microfluidic substrate.

The microfluidic system of FIG. 7 was fabricated using the method described in Example 1. This system included four sections: a reagent storage area, a sample loading area, an immunoassay area and a waste area. The reagent storage area was pre-filled with reagents required to perform an immunoassay for the detection of total human IgG in whole blood: antibody solutions, washing buffers and amplification reagents (either enzymatic substrates or silver amplification reagents) using the method described in Example 2. These reagents were presented as ready-to-use aqueous solutions loaded as a sequence of liquid plugs, separated from each other by air gaps.

A sample of blood from a donor was obtained and the sample was loaded into a capillary tube (e.g., as shown in FIG. 8A) by capillary forces (or, in other experiments, by aspirating the sample in the capillary tube using a negative pressure applied at the other end of the tube). The outlet of the capillary tube was fitted to the sample loading port of the substrate and the sample was introduced into the microfluidic system by moving the frit within the tube towards the end of the capillary tube with a plunger. Because the reagent inlet of the microfluidic substrate had been previously sealed, the flow of sample was automatically directed inside the microfluidic channel towards the outlet of the device, which was vented. The capillary was left in place, and the frit (now wetted with sample) acted as an air-tight seal.

After introducing the sample into the substrate, the seal over the inlet and outlet ports were removed. Application of vacuum at the outlet of the system resulted in the delivery of the sample and the reagents to the immunoassay area according to the sequence pre-defined by the order of reagents lined up inside the reagent storage area. All fluids exiting the immunoassay area were eventually trapped inside the waste area. After completion of the assay, a signal specific for the target analyte was observable in the immunoassay areas.

EXAMPLE 4

Performing an Immunoassay by Loading a Sample Using a Fluidic Connector

This example shows that an immunoassay can be performed by loading a sample using a fluidic connector and using reagents stored on a microfluidic substrate.

The microfluidic system of FIG. 5 was fabricated using the method described in Example 1. Device 300 includes sections 302 containing wet stored reagents and section 350 containing stored dry reagents. Immunoassay area 360 was prefabricated with physisorbed molecules using the method described in Example 2. The immunoassay area included a first detection zone 362 patterned with Tween (using a solution of Tween in PBS), second and third detection zones 364 and 366 patterned with anti-human IgG (using a solution of anti-human IgG in PBS), and a fourth detection zone 368 included patterned human IgG (using a solution of human IgG in PBS).

Figures 5A, 5B:
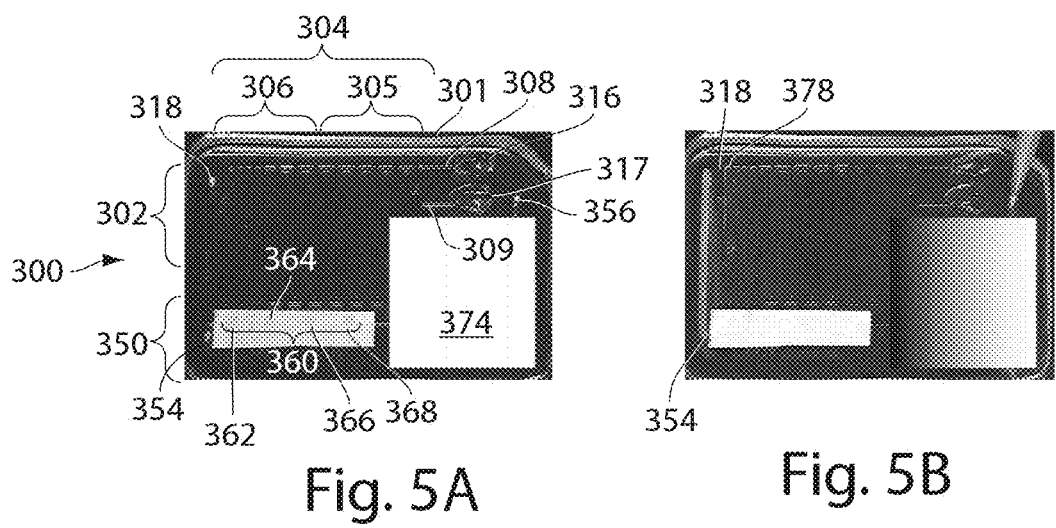
FIGS. 5A-5F are photographs of a microfluidic device including a fluidic connector used to perform a chemical and/or biological reaction according to an embodiment of the invention.

Reagent storage area 304 was pre-filled (using the method described in Example 2) with reagents required to perform an immunoassay for the detection of total human IgG in whole blood. The reagents were filled in the form of a sequence of liquid plugs, each of the liquid plugs separated by gaseous spacers. The reagents in lower portion 306 of the reagent storage area were (in order of introduction into the immunoassay area): three buffer washes, one plug of anti-human IgG labeled with gold colloid, three buffer washes, and six water washes. Upper portion 305 of the reagent storage area contained solutions for electroless silver deposition used as the amplification solutions. These solutions included silver salt, stored in channel 308, and hydroquinone, stored in channel 309. These solutions were kept separate prior to use. In FIG. 5A, the inlet 354 and outlet 318, which had previously been sealed, were unsealed at this stage.

A sample of venous blood from a healthy donor was obtained and the sample was loaded into a fluidic connector by capillary forces (or, in other experiments, by aspirating the sample in the capillary tube using a negative pressure applied at the other end of the tube). The fluidic connector was filled with a known, predetermined volume of sample (15 µL) by choosing an appropriate length of the capillary (and knowing the internal volume of the capillary). (This volume of sample was enough to sustain sample incubation for 10 minutes after the source of vacuum was set at −15 kPa.) The fluidic connector was bent so that one end of the fluidic connector fit into an outlet 318 of the reagent storage area, and the other end fit into an inlet 354 leading to the immunoassay area (see FIG. 5B). The fluidic connector enabled fluidic connection between sections 302 and 350. In FIG. 5A, inlets 316 and 317 and outlet 356, which had previously been sealed, were unsealed at this stage.

Figures 5C, 5D:
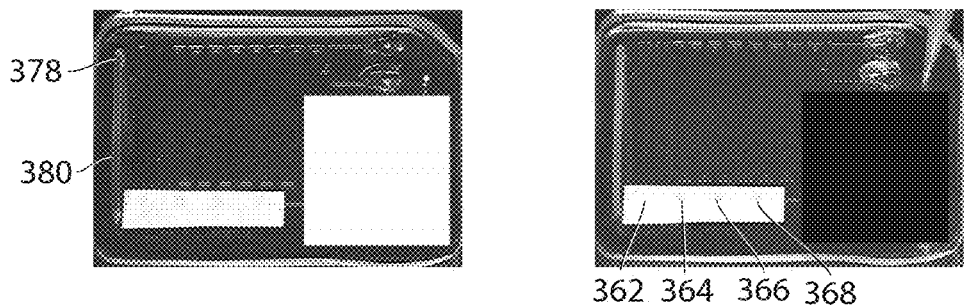

Application of a source of vacuum 390 (−15 kPa) at outlet 356 of the system initiated the assay. The sample entered the immunoassay area, including detection zones 362, 364, 366, and 368 (FIG. 5C), followed by the stored reagents from section 302 (FIG. 5D). The stored regents from section 302 included several rinsing reagents (e.g., buffer), which washed away any residual, unbound sample in the reaction area (FIG. 5D), as well as antibody solutions and amplification reagents.

Figures 5E, 5F:
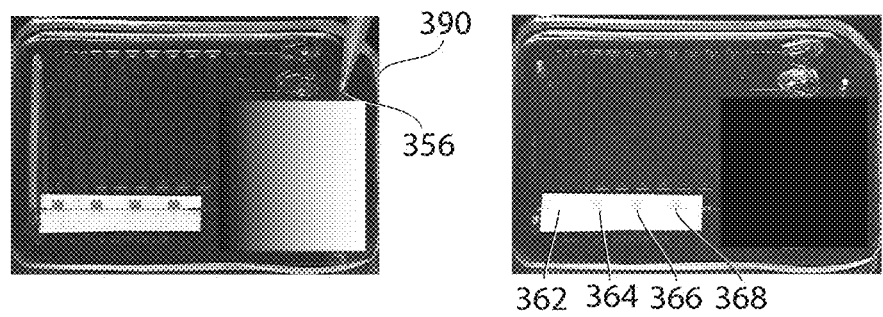

After completion of the assay, an optical signal (a grayish film of metallic silver) specific for the analyte of interest was observable in detection zones 364, 366, and 368 of the immunoassay area (FIG. 5E). Using the series of physiorbed biomolecules in the detection zones as described above, the following results were observed at the end of the assay: 1) no signal in the detection zone modified with Tween (a detergent known to prevent adhesion of proteins), as this detection zone acts as an internal negative reference (detection zone 362); 2) a concentration-dependant signal in the detection zones modified with anti-human IgG, reflecting the binding of human IgG from the sample (detection zones 364 and 366); and 3) a constant signal in the detection zone modified with human IgG, which acts as an internal positive reference (detection zone 368). These observations were expected.

As shown in FIG. 5F, after removal of the fluidic connector and the source of vacuum, the signal remained permanently bound in the immunoassay area of the device, and could be directly observed and used for data storage.

This example demonstrates that a microfluidic system having stored reagents contained therein, connected by a fluidic connector containing a sample, can be used to detect total human IgG in a sample of whole blood.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:
in a fluidic device containing a first fluid, wherein the first fluid is stored in a region of the device that includes a fluid-tight seal, performing the steps of:
unsealing the fluid-tight seal;
introducing a sample into the fluidic device after the unsealing step by inserting a sample introduction component containing the sample into a port of the fluidic device, wherein the step of inserting the sample introduction component containing the sample into the port of the fluidic device causes the unsealing of the fluid-tight seal;
passing the sample across a reaction area of the fluidic device;
passing the first fluid across the reaction area; and
determining a component of the sample at the reaction area.

2. The method of claim 1, wherein the sample introduction component remains attached to the fluidic device during the steps of passing the sample and the first fluid across the reaction area.

3. The method of claim 1, wherein the fluid-tight seal is a cover on a port of the fluidic device.

4. The method of claim 3, wherein inserting the sample introduction component containing the sample into the port of the fluidic device causes the cover of the port to be pierced or broken.

5. The method of claim 1, wherein the step of introducing the sample into the fluidic device comprises applying a vacuum to an outlet of the fluidic device to cause the sample to flow from the sample introduction component into the fluidic device.

6. The method of claim 1, comprising passing the first fluid across the reaction area after the step of passing the sample across the reaction area.

7. The method of claim 1, wherein the fluid-tight seal is a piercable seal.

8. The method of claim 1, wherein the first fluid is stored in a microfluidic channel having at least one cross-sectional dimension of less than 1 mm.

9. The method of claim 1, wherein the first fluid is a wash fluid.

10. The method of claim 1, wherein the sample introduction component comprises an inlet and an outlet, the method comprising inserting both the inlet and outlet into ports of the fluidic device.

11. The method of claim 1, wherein the sample introduction component, when inserted into the port to the fluidic device, is downstream of the region containing the first fluid and upstream of the reaction area.

* * * * *